United States Patent
Matyjaszczyk et al.

(10) Patent No.: US 8,067,731 B2
(45) Date of Patent: Nov. 29, 2011

(54) CHEMICAL DETECTION METHOD AND SYSTEM

(75) Inventors: Maciej (Matthew) Stanislaw Matyjaszczyk, Monroe, NC (US); Amy Elizabeth Staubs, Monroe, NC (US)

(73) Assignee: Scott Technologies, Inc., Boca Raton, FL (US)

( * ) Notice: Subject to any disclaimer, the term of this patent is extended or adjusted under 35 U.S.C. 154(b) by 308 days.

(21) Appl. No.: 12/390,305

(22) Filed: Feb. 20, 2009

(65) Prior Publication Data

US 2009/0224150 A1 Sep. 10, 2009

Related U.S. Application Data

(60) Provisional application No. 61/068,515, filed on Mar. 8, 2008.

(51) Int. Cl.
*B01D 59/44* (2006.01)
*H01J 49/00* (2006.01)

(52) U.S. Cl. ......... 250/295; 250/299; 250/281; 250/282

(58) Field of Classification Search .......... 250/281–284, 250/287, 292–295, 299, 396 R, 397, 526
See application file for complete search history.

(56) References Cited

U.S. PATENT DOCUMENTS

| | | | |
|---|---|---|---|
| 7,399,959 B2 * | 7/2008 | Miller et al. | 250/287 |
| 7,714,284 B2 * | 5/2010 | Miller et al. | 250/295 |
| 7,902,498 B2 * | 3/2011 | Miller et al. | 250/282 |
| 2003/0020012 A1 | 1/2003 | Guevremont | |
| 2003/0038235 A1 | 2/2003 | Guevremont | |
| 2005/0161596 A1 | 7/2005 | Guevremont | |
| 2006/0222562 A1 * | 10/2006 | Miller et al. | 422/50 |
| 2006/0226353 A1 | 10/2006 | Tang et al. | |
| 2007/0158543 A1 * | 7/2007 | Clowers et al. | 250/282 |
| 2008/0149824 A1 * | 6/2008 | Miller et al. | 250/287 |
| 2008/0185512 A1 * | 8/2008 | Miller et al. | 250/287 |
| 2009/0152458 A1 * | 6/2009 | Vilkov et al. | 250/282 |
| 2009/0256073 A1 * | 10/2009 | Guo et al. | 250/288 |
| 2011/0042561 A1 * | 2/2011 | Miller et al. | 250/282 |

OTHER PUBLICATIONS

R. Timothy Short et al, Development of an In-Situ Mass Spectrometer for Stable Isotope Analysis, Grant No. N00014-02-1-0309, 5 pgs.

Griffin Analytical Technologies, Mass Spectrometry Mass Spectrometry (MS/MS), 2006-2008, 2 pgs.

(Continued)

*Primary Examiner* — Bernard E Souw
(74) *Attorney, Agent, or Firm* — Christopher R. Carroll; Small Patent Law Group, LLC

(57) ABSTRACT

A system and method for detecting an analyte of interest in a sample is provided. The method includes passing a set of ions obtained from the sample through an ion mobility spectrometer to filter out ions that are not ions of interest and to generate an ion mobility spectrum. A mass spectrum of at least some of the ions is generated using a mass spectrometer. The method also includes determining that the analyte of interest is in the sample when peaks of interest are found in one or more of the ion mobility spectrum and the mass spectrum, and the peaks of interest follow a predetermined pattern of peaks associated with the analyte of interest or are confirmed by ion mobility spectrometry.

22 Claims, 16 Drawing Sheets

OTHER PUBLICATIONS

John Houseman, et al, A Portable Universal Hazardous Gas Detector, 11 pgs.

Randy W. Purves, et al, Mass spectrometric characterization of a high-field asymmetric waveform ion mobility spectrometer, Review of Scientific Instruments, Vo. 69, No. 12, Dec. 1998, 12 pgs.

International Search Report, Scott Technologies, App. No. PCT/US2009/001464, 4 pgs.

Written Opinion of the International Searching Authority, Scott Technologies, App. No. PCT/US2009/001464, 8 pgs.

* cited by examiner

CHEMICAL DETECTION METHOD AND SYSTEM

CROSS-REFERENCE TO RELATED APPLICATIONS

This application relates and claims priority to U.S. Provisional Patent Application Ser. No. 61/068,515 (the '515 Application). The '515 application was filed on Mar. 8, 2008, and is entitled "Chemical Detection Method And System." The complete subject matter and disclosure of the '515 Application is incorporated by reference herein in its entirety.

BACKGROUND OF THE INVENTION

The subject matter herein generally relates to chemical detection systems and, more particularly, to chemical detection systems that include one or more ion mobility spectrometers and mass spectrometers.

Chemical detection systems are used to detect particular threats. These threats include explosives, illicit drugs, chemical warfare agents, pollutants, and toxins, for example. Many of these detection systems include ion mobility spectrometers. The ion mobility spectrometers measure the presence of ions obtained from analytes in a sample. The ions are created by ionizing vapor molecules from the sample. The sample is obtained in the form of vapors from ambient air or in the form of particulate matter from ambient air, a package, luggage or person that is being examined for explosives, drugs or other chemical agents.

The ions that are obtained from the analytes in the sample are represented as peaks on an ion mobility spectrum. The peaks in the spectrum are used to determine whether a particular ion of interest is present in the sample. An ion of interest is an ion that is associated with a particular analyte of interest. An analyte of interest is a chemical species that commonly is found with the explosives, drugs, chemical warfare agents, and other chemicals that are sought to be detected.

One problem associated with ion mobility spectrometers is the resolution of the spectrometers. In some cases, known spectrometers may have difficulty in distinguishing between chemicals present in the background of the sample and the analytes of interest. These devices can produce false positive and false negative alarms. A false positive alarm occurs when the spectrometer misinterprets a peak in a spectrum as representing a threat. A false negative alarm occurs when the spectrometer misinterprets a peak in a spectrum that corresponds to an analyte of interest as corresponding to an analyte that is not of interest. A false negative alarm also may occur when a peak of interest is suppressed or obscured by other peaks. These other peaks may be associated with other analytes in the sample that are not analytes of interest.

Thus, a need exists for an improved chemical detection system that more accurately detects the presence of one or more analytes of interest in a sample. Such a system can improve existing procedures for detecting explosives, illicit drugs, chemical warfare agents, toxins or pollutants.

BRIEF DESCRIPTION OF THE INVENTION

In one embodiment, a method for detecting an analyte of interest in a sample is provided. The method includes passing a set of ions obtained from the sample through an ion mobility spectrometer to filter out ions that are not ions of interest and to generate an ion mobility spectrum. A mass spectrum of at least some of the ions is generated using a mass spectrometer. The method also includes determining that the analyte of interest is in the sample when peaks of interest are found in one or more of the ion mobility spectrum and the mass spectrum and the peaks of interest follow a predetermined pattern of peaks associated with the analyte of interest. Optionally, the passing operation comprises passing the ions through a plurality of ion mobility spectrometers connected in series with one another. The peaks of interest may comprise one or more of a molecular peak created from ions associated with a molecule (monomer) in the analyte of interest, and its clusters, like dimers, trimers, etc, an ion fragment peak created from an ion fragment obtained from the analyte of interest, a dopant-related peak created from a chemical species formed from a reaction between the analyte of interest (monomer, dimer, trimer, etc. or its monomer fragments) and a dopant or any other peak(s) related to the analyte of interest, including the specific complexes between molecular, and fragments of the analyte of interest, and the high electron/proton affinity components of the matrix. In one embodiment, the method includes determining that the analyte of interest is in the sample when the peaks of interest include the molecular peak (at least one of the monomer, dimer, trimer, etc.) and at least one of the ion fragment or the dopant-related peaks or any other peak(s) related to the analyte of interest in the mass spectrum.

In another embodiment, a system for detecting an analyte of interest in a sample is provided. The system includes an ion mobility spectrometer, a mass spectrometer and a computing device. The ion mobility spectrometer is configured to receive a set of ions obtained from the sample to filter out ions that are not ions of interest and to generate an ion mobility spectrum. The mass spectrometer is connected in series with the ion mobility spectrometer to receive at least some of the ions from the ion mobility spectrometer and to generate a mass spectrum of the ions received from the ion mobility spectrometer. The computing device determines that the analyte of interest is in the sample when peaks of interest are found in one or more of the ion mobility spectrum and the mass spectrum and the peaks of interest follow a predetermined pattern of peaks associated with the analyte of interest or ion mobility peaks are confirmed. Optionally, the system includes at least one additional mass spectrometer connected in series with the ion mobility spectrometer and the mass spectrometer. In another embodiment, the system includes a series of field compensation ion mobility spectrometers connected to a single mass spectrometer. In another embodiment, a series of ion mobility spectrometers is connected to a series of mass spectrometers. The ions received by each of the mass spectrometer and the additional mass spectrometer are used to generate a mass spectrum. In one embodiment, the computing device determines that the analyte of interest is in the sample when the peaks of interest include the molecular peak and at least one of the ion fragment peak, the dopant-related peak, and any other peak(s) related to the analyte of interest in the mass spectrum, and the known peak pattern is followed.

In another embodiment, a computer-readable storage medium for a computing device configured to determine if an analyte of interest is in a sample is provided. The computer-readable storage medium includes instructions to direct the computing device to generate one or more of an ion mobility spectrum and a mass spectrum of ions obtained from the sample and detect peaks of interest in one or more of the ion mobility spectrum and the mass spectrum. The instructions also direct the computing device to determine if the peaks of interest follow a predetermined pattern of peaks associated with the analyte of interest and provide a notification that the analyte of interest is in the sample when the peaks of interest follow the predetermined pattern of peaks. Optionally, the instructions direct the computing device to provide the notification if a molecular peak of interest (e.g., monomer, dimer, trimer, etc.) and at least one of an ion fragment peak of interest and a dopant-related peak of interest (e.g. molecular-dopant or fragment-dopant) or any other peak(s) related to the analyte of interest are found in the mass spectrum. In one embodiment, the instructions direct the computing device to confirm the presence of the peak of interest by obtaining a portion of the peak of interest using a first electric field in the ion mobility spectrometer and obtaining an additional portion of the peak of interest using a second electric field in the ion mobility spectrometer.

In another embodiment, another system for detecting an analyte of interest in a sample is provided. The system includes first and second field compensation ion mobility spectrometers and a computing device. The first field compensation ion mobility spectrometer receives a set of ions generated from the sample to filter out ions from the set that are not ions of interest and/or generate a first ion mobility spectrum. The second field compensation ion mobility spectrometer is connected with the first FCIMS and receives ions from the first FCIMS to generate a second ion mobility spectrum, where the second electric field is at least four times higher than the first electric field. The computing device analyzes the first and second ion mobility spectra to determine a presence of the analyte of interest in the sample when peaks of interest are in one or more of the first and second ion mobility spectra. Optionally, the computing device determines the presence of the analyte of interest when the peaks of interest are confirmed in at least one of the first and second FCIMS. In one embodiment, each of the first and second field compensation ion mobility spectrometers comprise opposing electrode plates configured to generate an electric field through which the ions pass before being detected or filtered by the first and second field compensation ion mobility spectrometers. The electrode plates of the first field compensation ion mobility spectrometer are separated by a different distance than the electrode plates of the second field compensation ion mobility spectrometer.

DETAILED DESCRIPTION OF THE INVENTION

Figure 1:
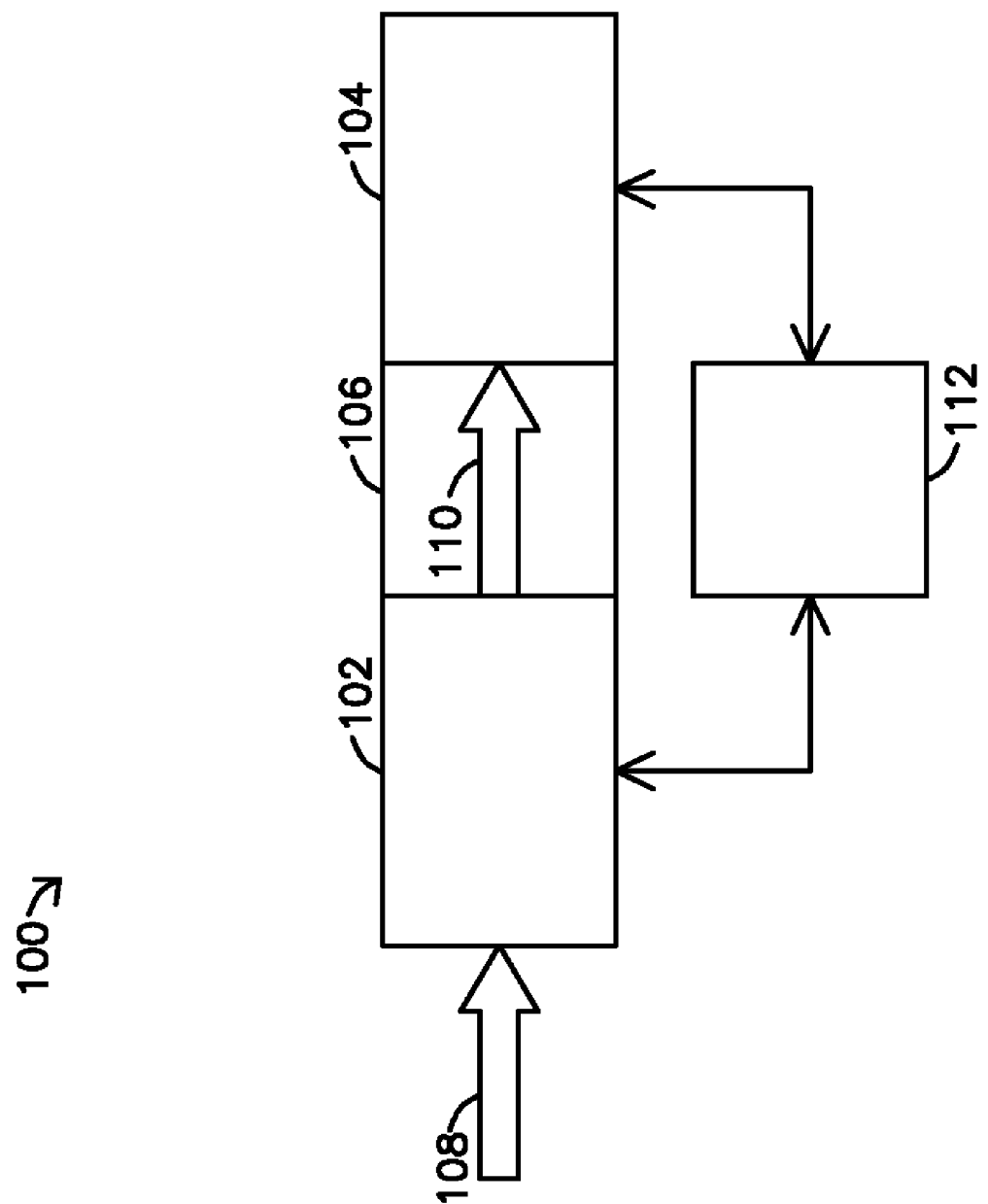
FIG. 1 is a schematic diagram of a chemical detection system according to one embodiment.

FIG. 1 is a schematic diagram of a chemical detection system 100 according to one embodiment. System 100 detects the presence of analytes of interest in a sample. The sample is obtained from a package or other object, air, or person. An analyte of interest is an analyte that is associated with a particular chemical or one or more explosives, illicit drugs, chemical warfare agents, industrial toxins, or environmental pollutants, for example. For example, certain chemical species are frequently found in locations proximate to explosive devices. These chemical species may be analytes of interest.

The detection system 100 includes a field compensation ion mobility spectrometer 102 interconnected with a mass spectrometer 104. The field compensation ion mobility spectrometer 102 is a spectrometer capable of ionizing analytes from a sample 108 to create a set of ions. In an exemplary embodiment, the field compensation ion mobility spectrometer 102 measures the presence of the ions in the set of ions to produce a spectrum 810 (shown in FIG. 8) of peaks (referred to as an ion mobility spectrum 810). As described below, the field compensation ion mobility spectrometer 102 creates the ion mobility spectrum 810 by passing the ions between electrode plates 316, 318 (shown in FIG. 3) that produce an electric field. Some ions are attracted to one of the plates 316, 318 while the remaining ions pass between the plates 316, 318 and are detected. The peaks represent the ions obtained from the various analytes in the sample. The identity of an analyte in the sample may be determined from one or more of the location of a peak on the ion mobility spectrum 810, the height of the peak, the width of the peak, and the shape of the peak, as well as from a pattern of peaks where multiple peaks are detected. An ion mobility spectrum 810 that is created for a particular sample 108 is the single or multipeak signature of the sample 108. Two or more ion mobility spectra 810 may be compared with one another to identify the analytes in the sample 108. Additionally, two or more ion mobility spectra 810 may be compared to confirm or verify the detection of an analyte in the sample 108.

The field compensation ion mobility spectrometer 102 filters out ions that are not of interest from the set of ions. For example, the field compensation ion mobility spectrometer 102 may filter out ions that are not ions of interest and provide an ion mobility spectrum 810 or the field compensation ion mobility spectrometer may filter out ions that are not ions of interest without providing an ion mobility spectrum 810. An ion of interest is an ion that is created from an analyte of interest. The remaining ions of interest in the set of ions are output from the field compensation ion mobility spectrometer 102 as a stream 110 of ions. An ion may be determined to be an ion of interest in the mass spectrometer 104 if the mass or the mass-to-charge ratio of the ion falls within a range of masses or range of mass-to-charge ratios which are of interest.

In an exemplary embodiment, the field compensation ion mobility spectrometer 102 detects the presence of only the ions of interest in the set of ions. The field compensation ion mobility spectrometer 102 reduces the amount of time required to create an ion mobility spectrum 810 for a particular sample 108 by only detecting the presence of the ions of interest instead of attempting to detect the presence of all ions obtained from the sample 108. The field compensation ion mobility spectrometer 102 detects the presence of the ions of interest after filtering out the ions which are not the ions of interest and prior to passing the set of one or more remaining ions in the stream 110 of ions. The field compensation ion mobility spectrometer 102 communicates the ion mobility spectrum 810 obtained from a sample 108 to a computing device 112.

The stream 110 of ions is passed from the field compensation ion mobility spectrometer 102 to a coupling 106. The coupling 106 interconnects the field compensation ion mobility spectrometer 102 with the mass spectrometer 104. The coupling 106 connects the field compensation ion mobility spectrometer 102 with the mass spectrometer 104 while maintaining the vacuum level in the mass spectrometer 104. The coupling 106 receives and focuses the stream 110 of ions. The coupling 106 then directs the stream 110 of ions into the mass spectrometer 104. In an exemplary embodiment, the coupling 106 includes an ion funnel. In another embodiment, the coupling 106 includes ion sampler and ion skimmer cones.

The mass spectrometer 104 receives the stream 110 of ions from the coupling 106. The mass spectrometer 104 measures the presence of the ions of interest in the set of ions. In an exemplary embodiment, the mass spectrometer 104 creates molecular and fragment ions and also detects their presence. For example, the mass spectrometer 104 may create additional ions by using electron impact, atmospheric pressure chemical ionization or other ionization methods on the stream 110 of ions and neutral sample molecules. The mass spectrometer 104 creates a spectrum 810 that represents the molecular ions and/or ion fragments, and/or dopant-related peaks, and/or and any other peak(s) related to the analyte of interest (referred to as a mass spectrum 810). The mass spectrum 810 is communicated to a computing device 112.

The computing device 112 receives the ion mobility spectrum 810 from the field compensation ion mobility spectrometer 102 and the mass spectrum 810 from the mass spectrometer 104. The computing device 112 then compares one or more peaks in the ion mobility and mass spectra 810 to determine if an analyte of interest is present in the sample 108. For example, the computing device 112 examines the mass spectrum 810 created by the mass spectrometer 104 to determine if one or more analytes of interest are in the sample 108. The computing device 112 examines both the ion mobility spectrum 810 produced by the field compensation ion mobility spectrometer 102 and the mass spectrum 810 produced by the mass spectrometer 104. The computing device 112 examines these spectra 810 to determine if one or more particular molecular peaks are present in each spectrum 810. If the computing device 112 determines that one or more particular molecular peaks are present in both spectra 810, then the computing device 112 determines that the analyte associated with that molecular peak in each spectrum 810 is present in the sample 108. In one embodiment, the molecular peaks include molecular peaks of interest and are peaks associated with one or more molecules found in the analyte of interest. The molecular peaks may include the molecular monomers, dinners, trimers, etc., as well as clusters of these species with other ions present in the ionization region of FCIMS, including dopant ions.

The computing device 112 may determine if one or more ion fragment peaks are in the mass spectrum 810. The ion fragment peaks include peaks that are obtained from fragments of the ions obtained from the analyte of interest in one embodiment. The fragments may be created in the mass spectrometer 104, as described below, and in FCIMS. In one embodiment, the ion mobility spectrum 810 may include one or more molecular peaks and one or more ion fragment peaks (or clusters of the ion fragment peaks with other ions in the ionization region) arranged in a pattern. The pattern in the ion mobility spectrum 810 includes the relative locations of the molecular and ion fragment peaks with respect to one another as well as the amplitudes or heights of the peaks in addition to the shape and width of the peaks. If a particular molecular peak is present in each of the ion mobility and mass spectra 810, one or more ion fragment peaks associated with particular ion fragments are found in the mass spectrum 810, and the pattern of the molecular and ion fragment peaks in the mass spectrum 810 is similar to the pattern of the molecular and ion fragment peaks in the mass spectrum 810 of an analyte of interest, then the computing device 112 determines that the analyte associated with those peaks is present in the sample 108.

One or more dopants may be introduced into the field compensation ion mobility spectrometer 102, as described below. The dopants may preferably combine, or otherwise react with, an analyte of interest in the sample 108. The combination or cluster of the dopant and the analyte of interest or of fragments of the analyte of interest and the dopant, or any other combination of the analyte of interest and the dopant may produce peaks in the ion mobility spectrum 810 that are referred to as dopant-related peaks. The computing device 112 determines that the analyte of interest is present in the sample 108 when the molecular peaks, the ion fragment peaks and one or more dopant-related peaks are present in the ion mobility spectrum 810 in one embodiment. Other peaks related to the analyte of interest may be present in the spectrum and the computing device 112 determines that the analyte of interest is present in the sample 108 when the molecular peaks, the ion fragment peaks, one or more dopant-related peaks or any other peaks related to the analyte of interest are present in the ion mobility spectrum 810 in one embodiment.

Alternatively, the detection system 100 may include two different field compensation ion mobility spectrometers interconnected with one another. For example, reference numbers 102 and 104 in FIG. 1 represent two different field compensation ion mobility spectrometers 102, 104. The field compensation ion mobility spectrometers 102, 104 may differ by having electrode plates 316, 318 (shown in FIG. 3) that are separated by different distances. For example, the first field compensation ion mobility spectrometer 102 may have electrode plates 316, 318 that are separated by a greater separation distance 330 (shown in FIG. 3) than the electrode plates 316, 318 of the second field compensation ion mobility spectrometer 104. One example of devices that may be used as the first and second field compensation ion mobility spectrometers 102, 104 include the microDMx™ sensor produced by Sionex Corp. as the first ion mobility spectrometer 102 and the FAIMS sensor used in Lonestar™ monitor or the Tourist™ test platform produced by Owlstone Nanotech, Inc. as the second ion mobility spectrometer 104. In another example, the sequence of the devices may be reversed.

The coupling 106 between the first and second field compensation ion mobility spectrometers 102, 104 does not maintain a vacuum between the first and second field compensation ion mobility spectrometers 102, 104 in one embodiment. For example, as a vacuum may not need to be established or maintained in either of the first and second field compensation ion mobility spectrometers 102, 104, the coupling 106 may not maintain any vacuum.

In another embodiment, the coupling 106 between the first and second field compensation ion mobility spectrometers 102, 104 does maintain a vacuum between the first and second field compensation ion mobility spectrometers 102, 104. For example, as a vacuum may need to be established or maintained in either of the first and second field compensation ion mobility spectrometers 102, 104 or both, the coupling 106 may have to maintain a vacuum.

In another embodiment, the coupling 106 between the first and second field compensation ion mobility spectrometers 102, 104 does maintain a higher pressure than the ambient pressure between the first and second field compensation ion mobility spectrometers 102, 104. For example, as a higher pressure than the ambient may need to be established or maintained in either of the first and second field compensation ion mobility spectrometers 102, 104 or both, the coupling 106 may have to maintain the higher pressure.

With the greater separation distance 330 between the electrode plates 316, 318, the first field compensation ion mobility spectrometer 102 may achieve lower electric fields between the plates 316, 318 while having improved resolution in discerning between the different ions in the sample when compared with the second field compensation ion mobility spectrometer 104. The first field compensation ion mobility spectrometer 102 may use this improved resolution relative to the second field compensation ion mobility spectrometer 104 to filter out ions that are not ions of interest before passing the remaining ions to the second field compensation ion mobility spectrometer 104. In contrast, the second field compensation ion mobility spectrometer 104 may produce substantially greater electric fields which can permit improved separation between specific ions in the sample, and the formation of new and specific ions which cannot be formed in the first field compensation ion mobility spectrometer 102. The second field compensation ion mobility spectrometer also filters out ions which are not ions of interest prior to gathering the second ion mobility spectrum. The combination of the specific peaks from the first field compensation ion mobility spectrometer 102, and from the second field compensation ion mobility spectrometer 104 may lead to an enhanced overall specificity of detection of analytes of interest in sample 108.

Figure 2:
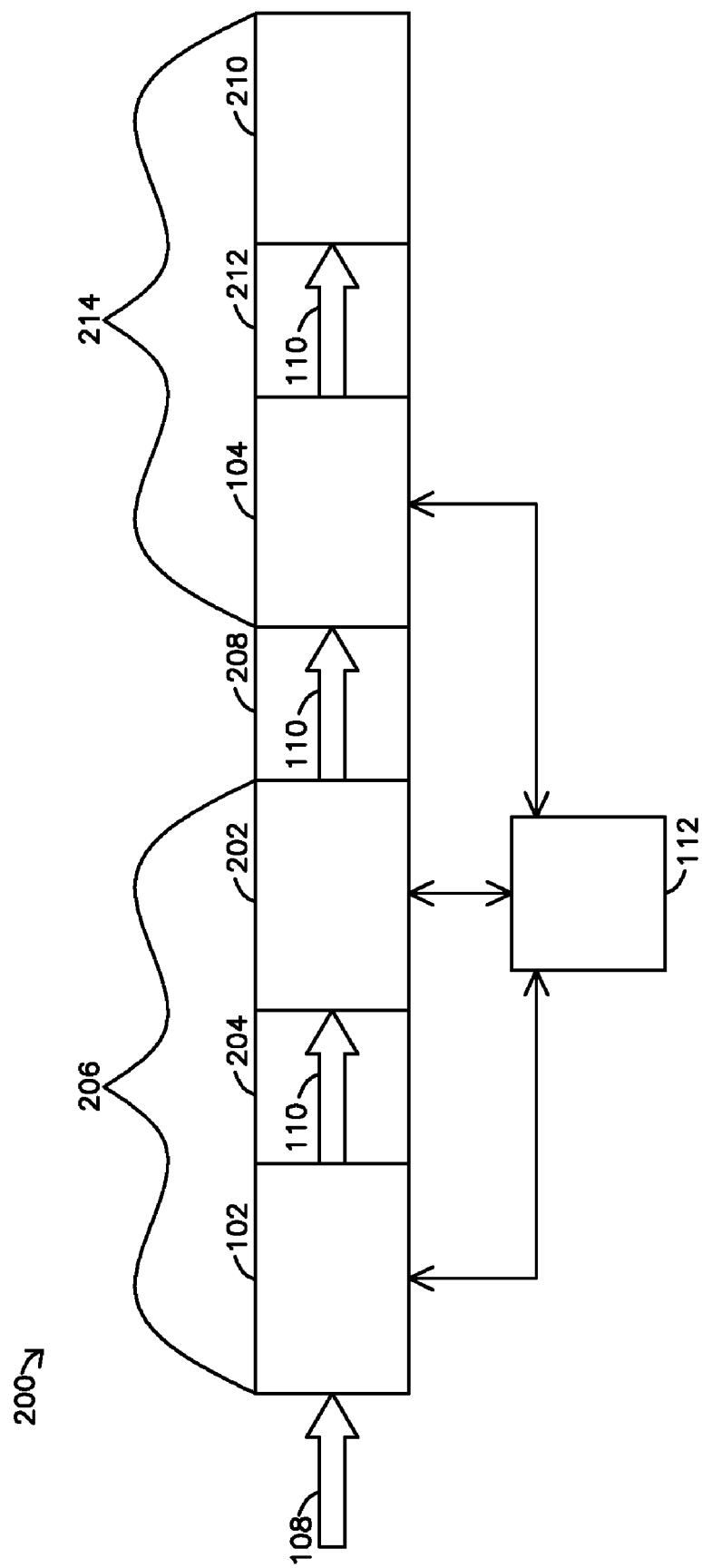
FIG. 2 is a schematic diagram of a chemical detection system according to another embodiment.

FIG. 2 is a schematic diagram of a chemical detection system 200 according to another embodiment. The detection system 200 is similar to the detection system 100 (shown in FIG. 1) with the addition of a series 206 of field compensation ion mobility spectrometers 102, 202 and a series 214 of mass spectrometers 104, 210. For example, a Cylindrical Ion Trap manufactured by Griffin Analytical Technologies, LLC may be used to couple the mass spectrometers 104, 210 with one another or series 214 may constitute a series of Cylindrical Ion Traps from Griffin. The series 206 includes two or more field compensation ion mobility spectrometers 102, 202 interconnected with one another. While two field compensation ion mobility spectrometers 102, 202 are shown in the series 206, the series 206 may include a larger number of field compensation ion mobility spectrometers 102, 202 interconnected in a series. Alternatively, the series 206 may include a single field compensation ion mobility spectrometer 102. The series 214 includes two or more mass spectrometers 104, 210 interconnected with one another. While two mass spectrometers 104, 210 are shown in the series 214, the series 214 may include a larger number of mass spectrometers 104, 210 or a single mass spectrometer 104.

A first coupling 204 interconnects adjacent ones of the field compensation ion mobility spectrometers 102, 202. In one embodiment, the coupling 204 is similar or the same as the coupling 106 (shown in FIG. 1). In another embodiment, the coupling 204 differs from the coupling 106 in that the coupling 204 does not maintain a vacuum in either of the field compensation ion mobility spectrometers 102, 202. Additionally, the series 206 of field compensation ion mobility spectrometers 102, 202 is interconnected with the mass spectrometer 104. The series 206 is interconnected with the mass spectrometer 104 through a second coupling 208. The second coupling 208 is similar to or the same as the coupling 106 and the first coupling 204. A third coupling 212 interconnects adjacent ones of the mass spectrometers 104, 210. In one embodiment, the coupling 212 is similar or the same as the coupling 106 (shown in FIG. 1).

In operation, the sample 108 is introduced into the first field compensation ion mobility spectrometer 102 in the series 206. As described above, the field compensation ion mobility spectrometer 102 obtains a set of sample molecules from the sample 108, ionizes them, generates an ion mobility spectrum 810, and determines the presence of one or more ions of interest in the ion mobility spectrum 810 (shown in FIG. 8). The ion mobility spectrum 810 is communicated to the computing device 112. In one embodiment, the field compensation ion mobility spectrometer 102 filters out at least some of the ions from the set of ions. The first field compensation ion mobility spectrometer 102 filters out at least some of the ions that are not ions of interest.

The first field compensation ion mobility spectrometer 102 then passes the ions in the stream 110 of ions to the second field compensation ion mobility spectrometer 202. The first field compensation ion mobility spectrometer 102 passes the stream 110 of ions to the second field compensation ion mobility spectrometer 202 through the coupling 204.

Similar to the first field compensation ion mobility spectrometer 102, the second field compensation ion mobility spectrometer 202 detects the presence of one or more ions of interest received from the stream 110 of ions to create a second ion mobility spectrum 810. The second ion mobility spectrum 810 is then communicated to the computing device 112. The second field compensation ion mobility spectrometer 202 also filters out at least some of the ions from the set. The second field compensation ion mobility spectrometer 202 filters out at least some of the ions that are not ions of interest. The second field compensation ion mobility spectrometer 202 then passes the remaining ions in the set in the stream 110 of ions to the mass spectrometer 104. The second field compensation ion mobility spectrometer 202 passes the stream 110 of ions to the mass spectrometer 104 through the coupling 208.

If the series 206 includes more than two field compensation ion mobility spectrometers 102, 202, then the second field compensation ion mobility spectrometer 202 passes the stream 110 of ions to the next field compensation ion mobility spectrometer in the series 206. Each of the field compensation ion mobility spectrometers in the series 206 filters out those ions that are not ions of interest and detects the presence of the ions of interest in an ion mobility spectrum 810. Additionally, each of the field compensation ion mobility spectrometers in the series 206 communicates an ion mobility spectrum 810 to the computing device 112. In one embodiment, all of the field compensation ion mobility spectrometers 102, 202 filter out ions that are not ions of interest but not all of them generate their ion mobility spectrum 810. For example, the first field compensation ion mobility spectrometer 102 may filter out ions that are not ions of interest without generating an ion mobility spectrum 810. The series 206 of field compensation ion mobility spectrometers 102, 202 may sequentially filter out ions that are not ions of interest before passing the remaining ions to a field compensation ion mobility spectrometer that creates an ion mobility spectrum 810 from the remaining ions. Alternatively, the first ion mobility spectrometer 102 may create an ion mobility spectrum 810 and then pass the ions to one or more additional ion mobility spectrometers 102, 202. The additional ion mobility spectrometers 102, 202 may filter out the ions that are not ions of interest and only the last ion mobility spectrometer 202 may generate an ion mobility spectrum 810. The remaining ions are then communicated to the mass spectrometer 104.

The series 214 of mass spectrometers 104, 210 receives ions from the series 206 of field compensation ion mobility spectrometers 102, 202. One or more of the mass spectrometers 104, 210 creates a mass spectrum 810 based on the ions received from the series 206 of field compensation ion mobility spectrometers 102, 202, and/or created in the first mass spectrometer from the neutral sample molecules. Similar to the field compensation ion mobility spectrometers 102, 202, one or more of the mass spectrometers 104, 210 may filer and/or create a mass spectrum 810 of the ions. For example, the first mass spectrometer 104 may filter out ions that are not ions of interest and create a mass spectrum 810. The second mass spectrometer 210 may then further filter out ions that are not ions of interest and create another mass spectrum 810. In another example, the first mass spectrometer 104 may filter out ions that are not ions of interest but not create a mass spectrum 810. The second mass spectrometer 210 then generates the mass spectrum 810.

One or more of the ion mobility spectra 810 created by the field compensation ion mobility spectrometers 102, 202 in the series 206 and one or more of the mass spectra 810 created by the mass spectrometers 104, 210 in the series 214 may be used by the computing device 112 to determine or verify that a particular analyte is in the sample 108. In an alternative embodiment, the detection system 200 does not include the series 214 of mass spectrometers 104, 210. For example, the detection system 200 includes a plurality of field compensation ion mobility spectrometers 102, 202 interconnected by one or more couplings 204. The field compensation ion mobility spectrometers 102, 202 each create an ion mobility spectrum 810 of the ions received by each spectrometer 102, 202. Each spectrometer 102, 202 then reports the spectrum 810 to the computing device 112. One or more of the spectra 810 created by the field compensation ion mobility spectrometers 102, 202 in the series 206 may be used by the computing device 112 to determine or verify that a particular analyte is in the sample 108.

Alternatively, the detection system 200 may include two different field compensation ion mobility spectrometers in the series 206. For example, the reference numbers 102 and 202 in FIG. 2 may represent two different field compensation ion mobility spectrometers 102, 202. The field compensation ion mobility spectrometers 102, 202 may differ by having electrode plates 316, 318 (shown in FIG. 3) that are separated by different separation distances 330, as described above and similar to the first and second field compensation ion mobility spectrometers 102, 104 shown in FIG. 1. The coupling 204 between the first and second field compensation ion mobility spectrometers 102, 202 may be similar to the coupling 106 (shown in FIG. 1). The series 206 of the first and second field compensation ion mobility spectrometers 102, 202 may be coupled with one or more mass spectrometers 104 in the series 214, as described above or may be used without the mass spectrometer(s) as 102, 104 in FIG. 1

Figure 3:
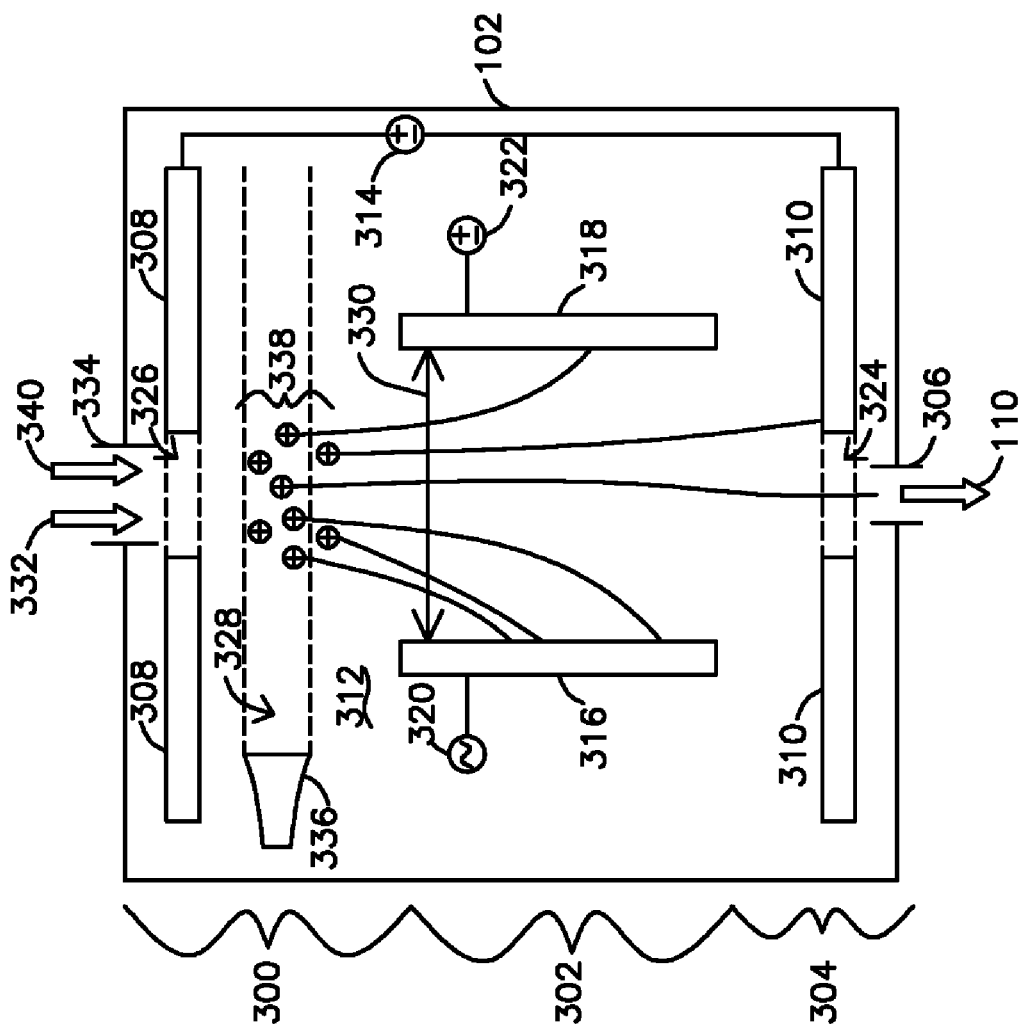
FIG. 3 is a schematic diagram of a field compensation ion mobility spectrometer shown in FIG. 1.

FIG. 3 is a schematic diagram of the field compensation ion mobility spectrometer 102 of FIG. 1. In one embodiment, the field compensation ion mobility spectrometer 102 is a miniaturized field ion spectrometer ("FIS"), a transverse field compensation ion mobility spectrometer ("TFC-IMS"), a differential mobility spectrometer ("DMS") or a high-field asymmetric waveform ion mobility spectrometer ("FAIMS"). For example, the field compensation ion mobility spectrometer 102 may be the microDMx™ sensor produced by Sionex Corp., the FAIMS sensor used in the Lonestar™ monitor, or the Tourist™ test platform, both produced by Owlstone Nanotech, Inc.

The field compensation ion mobility spectrometer 102 detects the presence of ions of interest in the set of ions obtained from the sample 108. As described above, the field compensation ion mobility spectrometer 102 filters out at least some ions that are not ions of interest from the set of ions. The field compensation ion mobility spectrometer 102 filters and detects ions by passing the ions through a filtering stage 302 and a collecting stage 304. At least some of the ions that are not ions of interest may be filtered out in the filtering stage 302. A portion of the ions of interest is collected and detected by the field compensation ion mobility spectrometer 102 on the collector 310 at the collecting stage 304 and at least some of the remaining portion is passed to the coupling 106 as the stream 110 of ions through an outlet 306. Alternatively, approximately none of the ions are detected by the collector 310 and substantially all of the ions pass to the coupling 106 as the stream 110 of ions. For example, the collector 310 may be modified in the field compensation ion mobility spectrometer 102 to permit all of the ions that are not filtered by the field compensation ion mobility spectrometer 102 to pass through to the coupling 106 as the stream 110 of ions.

The field compensation ion mobility spectrometer 102 includes an interior 312 disposed between the inlet 334 and the outlet 306. The interior 312 is divided into three stages: an ionizing stage 300, the filtering stage 302 and the collecting stage 304. The ionizing stage 300 includes an ionization device 336. The ionization device 336 is a device or apparatus that ionizes a gas sample 340 to create a set of ions, such as positive ions 338, for example. The gas sample 340 is at least a portion of the analytes in the sample 108 in the gas phase. The analytes in the sample 108 can be converted to the gas phase by heating the sample 108 to vaporize the analytes. The gas sample 340 may be introduced into the ionization stage 300 through the inlet 334. In an exemplary embodiment, the ionization device 336 is a corona discharge needle. Alternatively, the ionization device 336 may be a radioactive source, an ultraviolet lamp or a Direct Analysis in Real Time ("DART") ion source. An example of a radioactive source is $^{63}$Ni. While the ions 338 are referred to as positive ions 338, positive and negative ions can be formed in the ionization device 336 based on, among other things, what ionization device is used to ionize the gas sample 340.

The ionizing stage 300 also includes a first detection electrode 308 connected to a first direct current ("DC") source 314. The first detection electrode 308 and a second detection electrode 310 apply an electric field across at least a portion of the interior 312 of the field compensation ion mobility spectrometer 102. This electric field drives ions 338 towards the second detection electrode 310. In one embodiment, the gas sample 340 may flow into the field compensation ion mobility spectrometer 102 such that the gas sample 340 flows through the field compensation ion mobility spectrometer from the first detection electrode 308 and toward the second detection electrode 310. In such an embodiment, both the electric field and the flow of the gas sample 340 may drive the ions 338 toward the second detection electrode 310. The first detection electrode 308 includes an opening 326. The opening 326 permits the gas sample 340 to pass through the first detection electrode 308.

By way of example only, the filtering stage 302 includes at least two parallel electrode plates 316 and 318 separated by a separation distance 330. The filtering stage 302 may include several more electrode plates 316, 318. A first electrode plate 316 is connected to an alternating current ("AC") source 320. The AC source 320 applies an asymmetric AC waveform to the first electrode plate 316. The set of voltages applied to the first electrode plate 316 by the AC source 320 is the dispersion voltage. As described below, the dispersion voltage causes some ions 338 to drift towards and combine with either the first or second electrode plates 316, 318 as the ions 338 move towards a collector electrode 310.

A second electrode plate 318 is connected to a second DC source 322. The second DC source 322 applies a direct current to the second electrode plate 318. The voltage applied to the second electrode plate 318 by the DC source 322 is the compensation voltage. As described below, the compensation voltage prevents some ions 338 from drifting towards and combining with the first or second electrode plates 316, 318 as the ions 338 move towards the collector electrode 310. Alternatively, the second DC source 322 is connected to the first electrode plate 316 instead of the second electrode plate 318.

The collecting stage 304 includes the second detection electrode 310. The second detection electrode 310 collects the ions of interest obtained from the sample 108, as described below. In an embodiment, the second detection electrode 310 is a Faraday plate. The second detection electrode 310 includes an opening 324. The opening 324 permits some of the ions 338 to pass through the second detection electrode 310 without being detected on 310.

In operation, the gas sample 340 is introduced into the ionizing stage 300 through the inlet 334 and the opening 326 in the first detection electrode 308. The gas sample 340 is ionized by the ionization device 336. The ionization device 336 emits energy 328 to form reactant ions which in turn ionize the gas sample 340. A set of ions 338 is created by ionizing the gas sample 340. In another embodiment, the ionization device 336 emits energy 328 which ionizes the gas sample 340 directly without the use of reactant ions.

In one embodiment, one or more dopants 332 are introduced into the ionizing stage 300 through the inlet 334, as referred to above. The dopants 332 are chemical species with a high electron or proton affinity in one embodiment. When the dopants 332 are introduced into the ionizing stage 300, the dopants 332 are ionized and then cluster or chemically react with analytes in the gas sample 340. For example, the ions of dopants 332 may react with neutral analytes of interest. The reaction between the ions of dopants 332 and analytes of interest may create larger ions with larger masses. These ions may have a different mass and/or mass-to-charge ratio than the ions produced by the direct ionization of the original analyte. In one embodiment, the dopants 332 do not react with analytes that are not analytes of interest; therefore preventing the ionization of interferences, and false alarms. For example, the dopants 332 may not preferably react with analytes that are not analytes of interest and produce ions that interfere with the detection of ions of interest in the field compensation ion mobility spectrometer 102.

In one embodiment, the ions created from the combination of the dopant 332 and an analyte of interest appear as peaks within a well defined narrow range (a window) of compensation voltages for a given dispersion voltage. Thus, the dopant 332 may be used as a type of marker for a particular ion of interest. As these ions may appear at known compensation voltages for a given dispersion voltage, the locations of the peaks associated with these ions on a spectrum also will be known in one embodiment.

The electric field generated by the first and second detection electrodes 308, 310 and the flow of the gas sample 340 drive the ions 338 from the ionizing stage 300 into the filtering stage 302. The ions 338 move between the first and second electrode plates 316, 318. An asymmetric AC waveform, or dispersion voltage, is applied to the first electrode plate 316 by the AC source 320. Additionally, the compensation voltage is applied to the second electrode plate 318 or the first electrode plate 316 by the second DC source 322.

Figure 4:
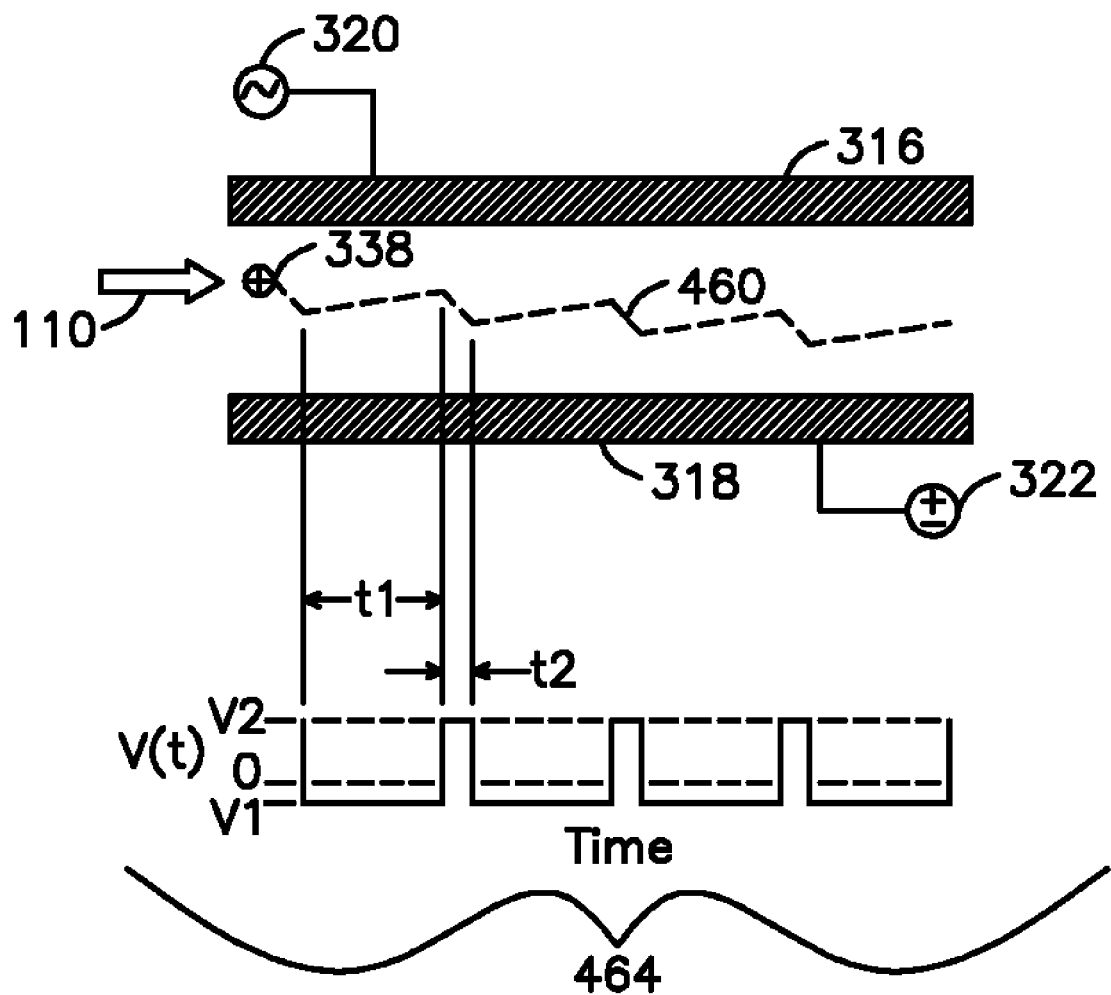
FIG. 4 is a schematic cross-sectional diagram of a positive ion moving between first and second electrode plates in a filtering stage shown in FIG. 3.

FIG. 4 is a schematic cross-sectional diagram of a positive ion 338 moving between the first and second electrode plates 316, 318 in the filtering stage 302 of FIG. 3. An arrow 110 represents the direction of flow of the ions 338 and the gas sample 340 between the first and second electrode plates 316, 318. A graph 464 in FIG. 4 provides a simplified representation of the asymmetric AC waveform that the AC source 320 applies to the first electrode plate 316. The asymmetric AC waveform in graph 464 includes a first voltage component V1 that lasts for a first time period t1 followed by a second voltage component V2 that lasts for a second time period t2. The asymmetric AC waveform repeats these components and time periods in a cyclic manner. For each complete cycle, the integrated field-time product is zero. For example, the sum of the product of V1 and t1 and the product of V2 and t2 is zero.

The first and second voltage components V1, V2 are of opposite polarities. For example, the first voltage component V1 is a negative voltage while the second voltage component V2 is a positive voltage. The first time period t1 is greater than the second time period t2. In one embodiment, the amplitude of the second voltage component V2 is greater than the amplitude of the first voltage component V1. For example, the asymmetric waveform may comprise a second voltage component V2 of +2000 V per separation distance 330 for a second time period t2 of 10 microseconds and a first voltage component of −1000 V per separation distance 330 for a first time period t1 of 20 microseconds. In another example, the difference in voltages between the first and second voltage components V1, V2 exceeds 20,000 V/cm of the separation distance 330. The difference may reach value of 100,000 V/cm of the separation distance 330 for the FAIMS sensor produced by Owlstone Nanotech, Inc.

Figure 5:
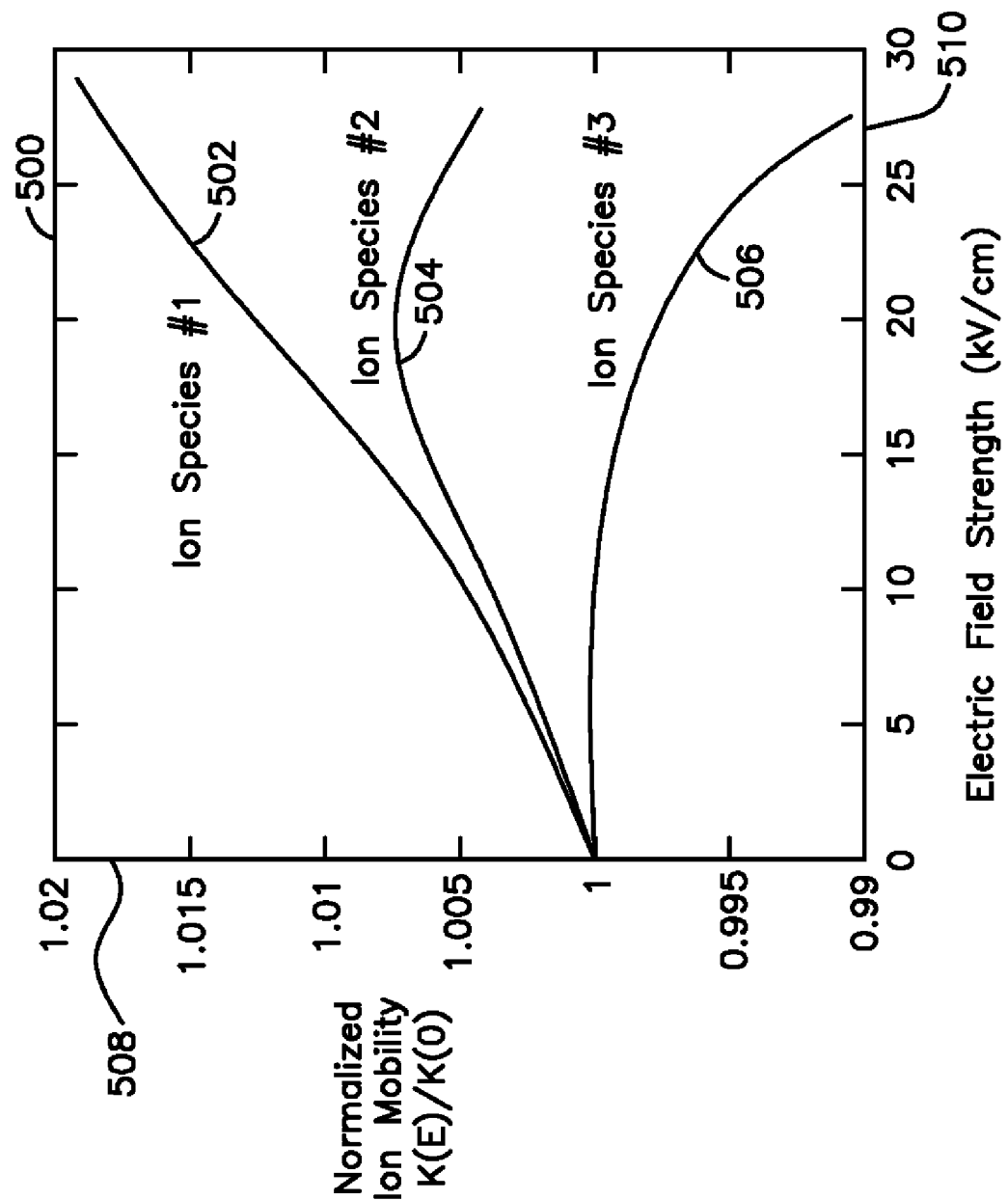
FIG. 5 is a graph that provides an ion mobility curve for each of three ion species at various electric field strengths.

With continued reference to FIG. 4. FIG. 5 is a graph 500 that provides ion mobility curves 502, 504, and 506 for each of three ion species at various electric field strengths. The graph 500 includes a vertical axis 508 and a horizontal axis 510. The vertical axis 508 represents a normalized mobility of an ion. The horizontal axis 510 represents a range of electric field strengths, expressed in kilovolts per centimeter. The ion mobility curves 502, 504, and 506 illustrate the dependence of an ion's mobility on the strength of the electric field. For example, a first ion species whose mobility is represented by the ion mobility curve 502 has a greater mobility that increases with increasing electric field strength. Additionally, the first ion species has a mobility that is greater than the mobility of a second and a third ion species (each having a mobility represented by one of the ion mobility curves 504, and 506, respectively) at greater electric field strengths. Conversely, the third ion species (whose mobility is represented by the ion mobility curve 506) has a lesser mobility at greater electric field strengths and has a mobility that decreases as the electric field strength increases.

The effects of the asymmetric AC waveform on a positively charged ion 338 travelling between the first and second electrode plates 316, 318 are represented by a path 460 in FIG. 4. The path 460 represents the displacement of the positively charged ion 338 with respect to the first and second electrode plates 316, 318. During the first time period t1, the positively charged ion 338 is attracted towards the first electrode plate 316. During the first time period 11, the voltage component V1 that is applied to the first electrode plate 316 is a negative voltage. The distance that the ion 338 is displaced depends on the mass, charge and shape of the ion 338. A smaller mass and/or greater charge of the ion 338 may cause the ion 338 to be displaced farther towards the first electrode plate 316 than another ion 338 with a larger mass and/or smaller charge.

At the end of the first time period t1, the voltage applied to the first electrode plate 316 changes to the second voltage V2. The second voltage V2 is applied for the second time period 12. As the second voltage V2 is a positive voltage, the positively charged ion 338 is repelled away from the first electrode plate 316. The positively charged ion 338 is repelled at a greater rate during the second time period t2 than the first time period t1. For example, the ion 338 moves away from the first electrode plate 316 at a faster rate because the magnitude of the second voltage V2 is greater than the magnitude of the first voltage V1. Despite the fact that $V_1 t_1 + V_2 t_2 = 0$, the displacement of ion 338 during t2 period will depend on the ion's mobility at the high voltage V2. For example, as described above and illustrated in the graph 500 of FIG. 5, different high electric fields can cause different ion species to have differing mobilities with respect to one another. As a result, the ions of different analytes will experience different displacements between the first and second electrode plates 316, 318. This phenomenon of ions reaching specific mobilities does not occur at low electric field strengths where mobilities of all species are the same, FIG. 5. In order to prevent ions associated with particular analytes from recombining with the first or second electrode plate 316, 318, different compensation voltages are applied to the second electrode plate 318. The ion 338 is repelled away from the first electrode plate 316 until the next first time period t1 begins and the first voltage V1 is once again applied to the first electrode plate 316.

The asymmetric AC waveform applied to the first electrode plate 316 causes the ion 338 to experience a net displacement, or drill, towards the second electrode plate 318. If the ion 338 is permitted to be displaced far enough, the ion 338 will migrate to and combine with the second electrode plate 318. If the ion 338 combines with the second electrode plate 318, the ion 338 docs not reach collecting stage 304 (shown in FIG. 3). If the ion 338 does not reach the collecting stage 304, the ion 338 is not measured or detected by the field compensation ion mobility spectrometer 102 and also does not exit the field compensation ion mobility spectrometer 102 through the outlet 306.

In order to prevent the ion 338 from combining with the second electrode plate 318, the compensation voltage is applied to the electrode plate 316 or 318. For example, if the asymmetric AC waveform causes the positively-charged ion 338 to drift towards the second electrode plate 318, a positive voltage is applied to the second electrode plate 318 (or a negative voltage applied to the first electrode plate 316) to drive the ion 338 back towards the first electrode plate 316. This compensation voltage reverses or compensates for the drill of the ion 338 towards the second electrode plate 318. Ions 338 may reach the collecting stage 304 if the compensation voltage prevents the ions 338 from combining with the second electrode plate 318.

The magnitude of the compensation voltage necessary to prevent the ions 338 from drifting towards and combining with the second electrode plate 318 varies for different ions 338. In order to obtain a spectrum of the various ions 338 from the gas sample 340, the compensation voltage applied to the second electrode plate 318 is scanned, or varied across a range of voltages. For example, the compensation voltages can be scanned from −50 to 0 V or from 0 V to +50 V. In another example, the compensation voltages may be scanned from −5 to 0 V or from 0 to +5V. For a given compensation voltage, a subset of the ions 338 will travel through the filtering stage 302 and not combine with the second electrode plate 318. When the subset of ions 338 does not combine with the second electrode plate 318, the ions 338 may reach the collecting stage 304.

Additionally, the asymmetric AC waveform that is applied to the first electrode plate 316 may be varied to prevent particular ions 338 from combining with the second electrode plate 318 and to increase the separation between the peaks of different analytes. In order to obtain a spectrum of the various ions in 338 set, the asymmetric AC waveform may be varied but may remain constant during a given analysis. The waveform can be varied by increasing or decreasing one or more of the first and second voltage components V1, V2 and the first and second time periods t1, t2. Additionally, the waveform can be varied by changing the polarity of one or both of the first and second voltage components V1, V2. As one or more of the first and second voltage components V1, V2 and the first and second time periods t1, t2 are changed, different ions 338 pass through the filtering stage 302 to the collecting stage 304.

Once an ion 338 reaches the collecting stage 304 (shown in FIG. 3), the ion 338 is either collected on the second detection electrode 310 or passes through the opening 324 in the second detection electrode 310. A current is generated by the ions 338 as the ions 338 are collected on the second detection electrode 310. As the number of ions 338 collected on the second detection electrode 310 increases, the current increases. The field compensation ion mobility spectrometer 102 can create a spectrum of the ions 338 collected on the second detection electrode 310 based on the current created by the ions 338. As the number of ions 338 reaching the second detection electrode 310 increases, the larger a corresponding peak in the spectrum becomes. The ions 338 that pass through the second detection electrode 310 are passed into the coupling 106. In order to shorten the analysis time and to filter out ions 338 that are not associated with analytes of interest, only the compensation voltage values corresponding to the positions of the peaks associated with the ions of interest are applied to the first or the second electrode 316 or 318 in one embodiment.

Figure 6:
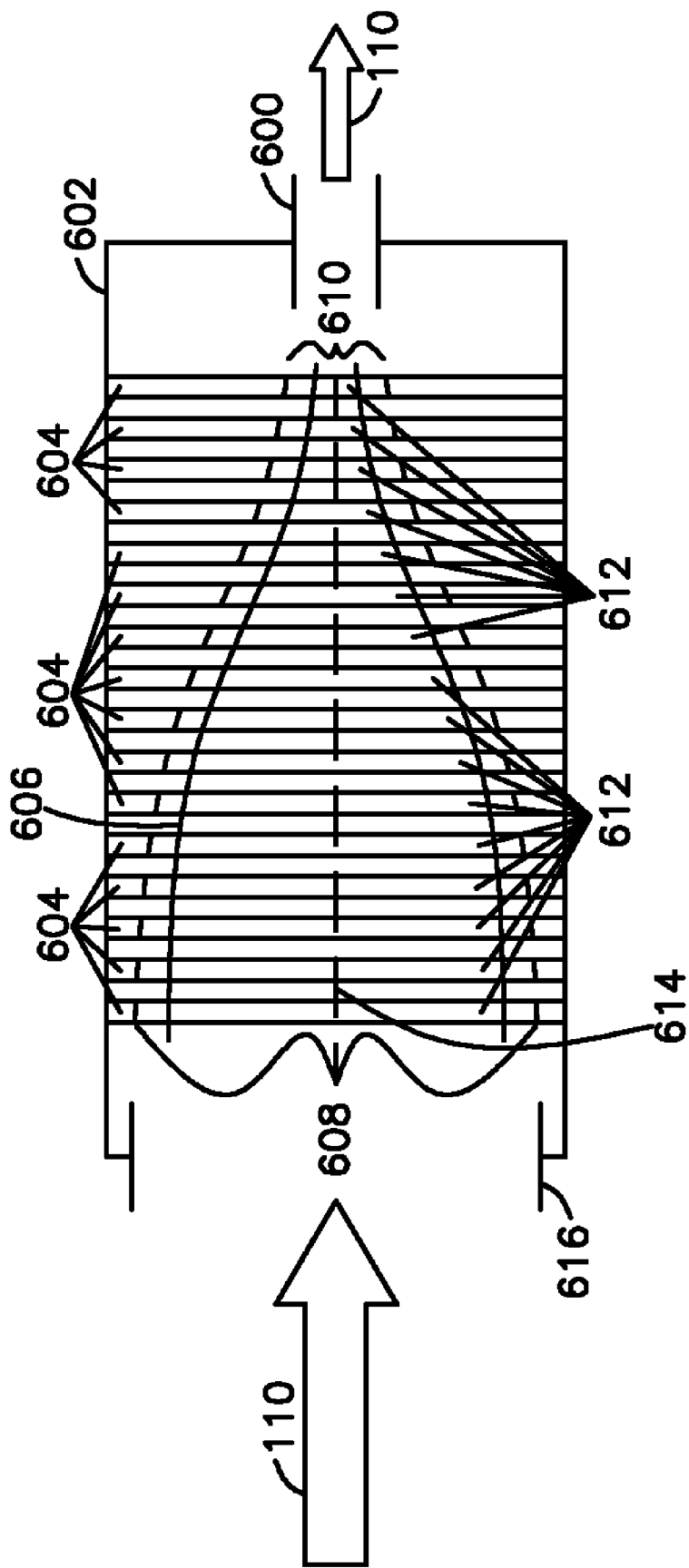
FIG. 6 is a schematic diagram of a coupling shown in FIG. 1.

FIG. 6 is a schematic diagram of the coupling 106 of FIG. 1. In the illustrated embodiment, the coupling 106 is an ion funnel. In another embodiment, the coupling 106 is a set of a sampler and ion skimmer cones. The coupling 106 includes a housing 602 that includes an inlet 616 and an outlet 600 on opposing sides of the housing 602. The stream 110 of ions is received into the housing 602 through the inlet 616. The housing 602 partially encloses a plurality of concentric ring-shaped electrodes 604. The electrodes 604 are disposed along a longitudinal axis 614 of the housing 602. Each of the electrodes 604 has an opening 612 through the center of the electrode 604. The size of the opening 612 in the electrodes 604 decreases in neighboring electrodes 604. For example, the electrode 604 nearest the inlet 616 has the largest opening 608 while the electrode 604 nearest the outlet 600 has the smallest opening 610.

In one embodiment, each of the electrodes 604 is a radio frequency ("RF") electrode. An alternating current is applied to each of the electrodes 604 to create a conductive path through the openings 612 in the electrodes 604 along the longitudinal axis 614. For example, the electrodes 604 may ionize the air or gas in the housing 602 and along the openings 612 to create a conductive path 606 along the longitudinal axis 614. The stream 110 of ions travels along the longitudinal axis 614 in the conductive path 606 from the inlet 616 towards the outlet 600. As the size of the openings 612 decreases in the electrodes 604, the size of the conductive path 606 also decreases. As the size of the conductive path 606 decreases, the size or diameter of the stream 110 of ions decreases. As a result, the size of the stream 110 of ions is decreased, or focused, as the stream 110 of ions enters the inlet 616 and exits the housing 602 through the outlet 600. As described above, the stream 110 of ions is passed from the outlet 600 to the mass spectrometer 104 (shown in FIG. 1).

Figure 7:
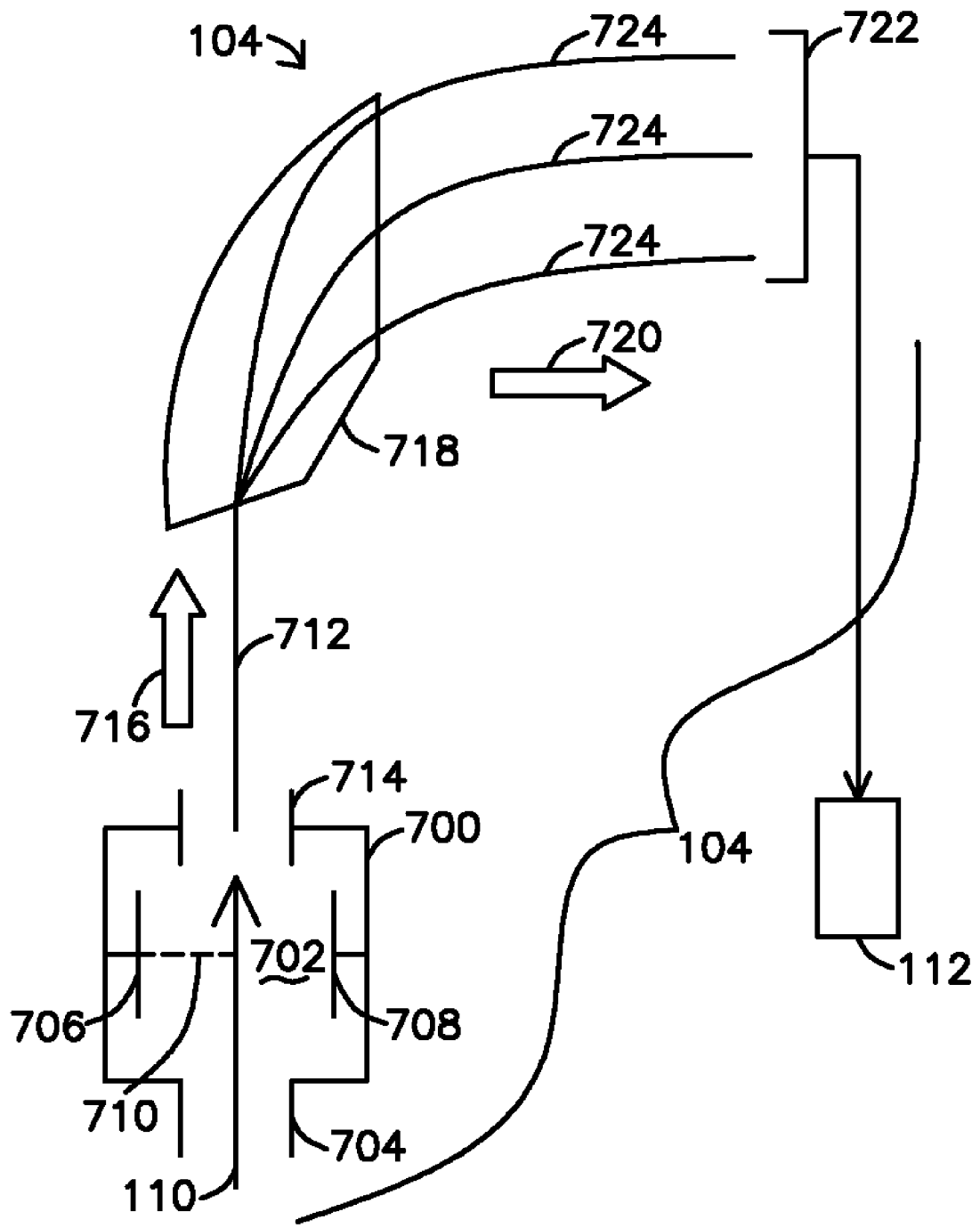
FIG. 7 is a schematic diagram of a mass spectrometer shown in FIG. 1.

FIG. 7 is a schematic diagram of the mass spectrometer 104 of FIG. 1. In one embodiment, the mass spectrometer 104 is a miniaturized mass spectrometer. Examples of a miniaturized mass spectrometer include the HAPSITE® Chemical Identification Systems produced by INFICON Holding AG, the CT-1128 Portable GC-MS produced by Constellation Technology Corp., the Ionchip® produced by Microsaic Systems Ltd., the miniature mass spectrometer, including the Ion-Camera™, by CMS Field Products. Division of O1 Analytical, and the Cylindrical Ion Trap or its series produced by Griffin Analytical Technologies, LLC. The mass spectrometer 104 may include an ion source 700. The ion source 700 includes an interior cavity 702 that receives the stream 110 of ions and neutral molecules from an inlet opening 704 of the ion source 700. In one embodiment, the inlet 704 is connected to the outlet 600 of the coupling 106 (shown in FIG. 1).

The ion source 700 may include an electron emitter 706 located within the cavity 702. The electron emitter 706 is a filament that is heated in a vacuum by running an electric current through the filament in one embodiment. As the electron emitter 706 is heated, electrons 710 are generated and emitted from the electron emitter 706 towards an anode 708 in the cavity 702. The electron emitter 706 and the anode 708 are positioned in the cavity 702 so that the stream 110 of ions and neutrals passes between the electron emitter 706 and the anode 708. The electrons 710 are emitted from the electron emitter 706 and pass through the stream 110 of ions and neutrals. As the electrons 710 pass through the stream 110 of ions, at least some of the electrons 710 strike neutrals and the ions 338 in the stream 110 and transfer energy of the electrons 710 to the neutrals and the ions 338. Alternatively, the stream 110 of ions may bypass the ion source 700 and only the neutral sample carrier gas 340 and neutral dopant(s) 332 of the ion stream 110 (shown in FIG. 3) are introduced into the ion source 700. The neutral sample carrier gas may then be ionized by the ion source 700 to create a new stream 110 of ions for the mass spectrometer 104 to analyze, together with the ions in the original stream 110 of FCIMS ions.

As the electrons 710 strike the neutrals and the ions 338, the neutrals and ions 338 may be fragmented and ionized. The molecular ion, ion fragments, dopant-related ions, and any other ion(s) related to the analyte of interest, original ions 338, and other ions) continue through the cavity 702 as an ion beam 712. The ion beam 712 exits the ion source 700 through an outlet 714 of the ion source 700. In another embodiment, no ion source 700 is used in mass spectrometer 104, and the ion stream 110, formed by the ion source(s) in the field compensated ion mobility spectrometers) 102, will be formed into the ion beam 712.

The ion beam 712 travels along a direction of travel 716 towards a magnetic field 718. The magnetic field 718 is generated by one or more magnets or electromagnets (not shown) in the mass spectrometer 104. The magnetic field 718 applies a force to each ion 338 and other ions in the ion beam 712. The force applied by the magnetic field 718 is in a direction 720. The direction 720 of the force applied by the magnetic field 718 is perpendicular to the direction of travel 716 of the ion beam 712. In another example, the mass spectrometer of a different type may be used which does not utilize the magnetic field to control the movement of ions.

The force applied by the magnetic field 718 deflects the ions 338 and other ions in the ion beam 712. This force causes the ions 338 and other ions to be deflected and alter the direction of travel 716 of the ions 338 and other ions. The amount of deflection in the direction of travel 716 for the ions 338 and other ions varies based on the mass-to-charge ratio and velocity of the ions 338 and other ions. The ions 338 and other ions with smaller masses are deflected more than the ions 338 and other ions with larger masses. Due to the varying masses of the ions 338 and other ions in the ion beam 712, the ion beam 712 is divided into a plurality of secondary ion beams 724. Each of the secondary ion beams 724 represents a different direction of travel of a group of the ions 338 and other ions that have the same or similar mass-to-charge ratio and velocity. Each of the secondary ion beams 724 strikes and is collected by a detector 722.

The detector 722 is a device that detects the presence of the ions 338 and other ions included in each secondary ion beam 724. The detector 722 measures the electric charge induced or current produced when the ions 338 and other ions in each of the secondary ion beams 724 contact a different location of the detector 722. The detector 722 detects the presence of the different ions 338 and other ions based on the location that the each secondary ion beam 724 strikes the detector 722 and the relative intensities of the electric charge induced or current produced by each secondary ion beam 724. The mass spectrometer 104 creates a spectrum 810 (shown in FIG. 8) based on the detection of the various ions 338 and other ions detected by the detector 722. The mass spectrometer 104 communicates the spectrum to the computing device 112. An example of the detector 722 includes a linear array charge-coupled device, also referred to as an ion-CCD or Ion-Camera™, offered by CMS Field Products, Division of O.I. Analytical. In another example, a different type of the mass spectrometer may be used with different type of detector.

Figure 8:
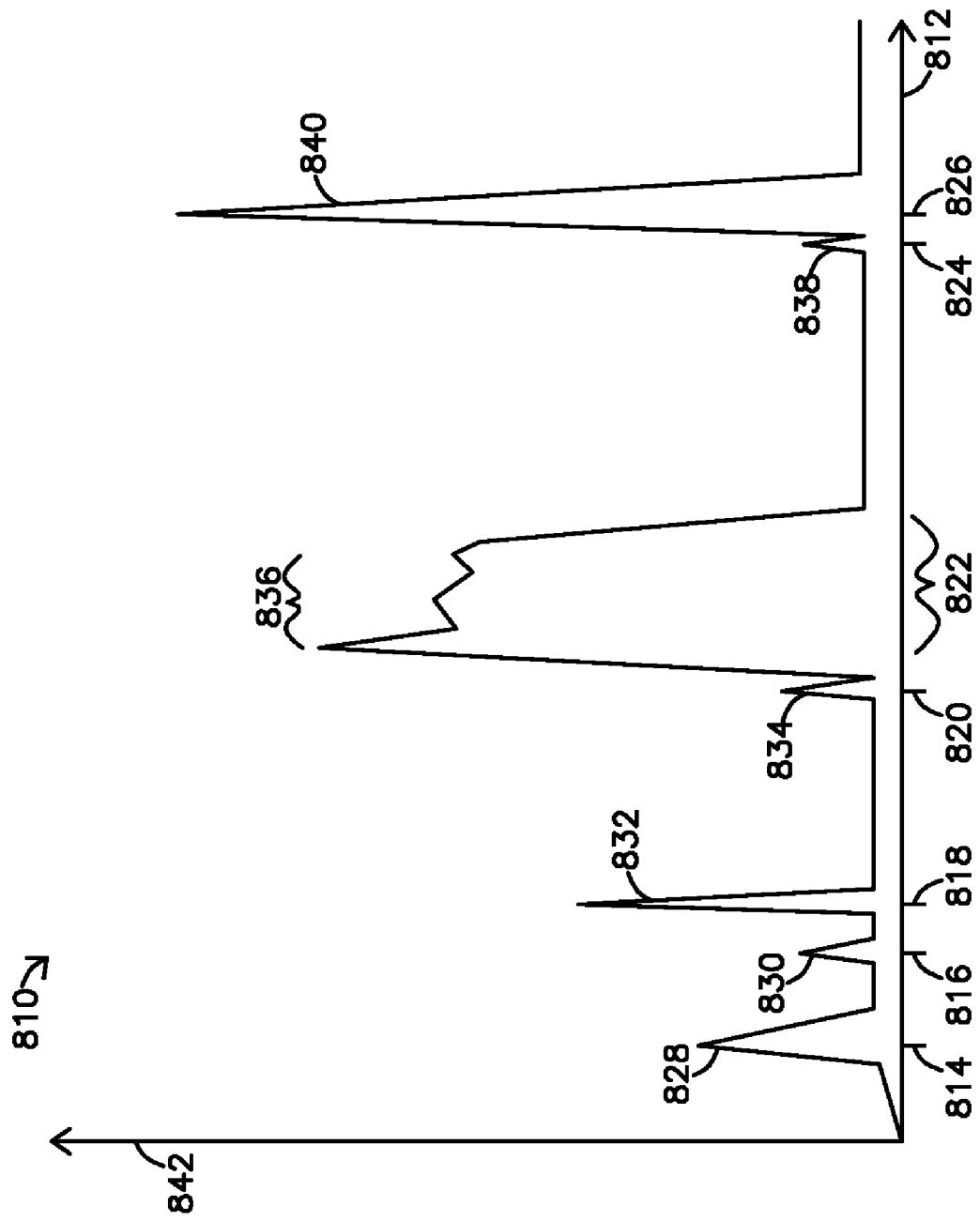
FIG. 8 is an exemplary embodiment of a spectrum generated by the field compensation ion mobility spectrometer or the mass spectrometer 104 of FIG. 1.

FIG. 8 is an exemplary embodiment of the spectrum 810 generated by the field compensation ion mobility spectrometer 102 or the mass spectrometer 104 of FIG. 1. As described above, the spectrum 810 represents the relative number of the various ions 338 and/or other ions measured by the field compensation ion mobility spectrometer 102 or the mass spectrometer 104. The relative number of each of the ions 338 and/or other ions is represented by one or a plurality of peaks 828 through 840.

The spectrum 810 is plotted along two axes 812, 842. The first axis 812 represents either the compensation voltage applied to the first 316 or second electrode plate 318 in the field compensation ion mobility spectrometer 102 (shown in FIG. 1) or the mass-to-charge ratios of the various ions 338 and other ions received at the detector 722 (shown in FIG. 7).

For example, for spectra 810 generated by the field compensation ion mobility spectrometer 102, the first axis 812 represents the compensation voltage applied to the first 316 or the second electrode plate 318. For spectra 810 generated by the mass spectrometer 104, the first axis 812 represents the mass-to-charge ratio of the ions 338 and other ions received at the detector 722 of the mass spectrometer 104. The second, or y, axis 842 represents the relative number of the various ions 338 and/or other ions measured by the field compensation ion mobility spectrometer 102 or the mass spectrometer 104.

The presence of various analytes in the sample 108 (shown in FIG. 1) can be determined by the presence of peaks associated with the analytes in the spectrum 810 at known locations along the first axis 812. For example, the peaks 828 through 840 could represent a series of analyte peaks with the height of the peaks 828 through 840 along the second axis 842. The ions 338 and other ions that are associated with or obtained from analytes of interest have one or more peaks 828 through 840 at a known position 814 through 826 along the first axis 812. For example, the location of the peak 832 for a first one of the ions 338 may be known to be at a location 818 on the first axis 812. The location of another peak 840 for a second one of the ions 338 may be known to be at a location 826.

Additionally, a location of a peak 828 through 840 along the first axis 812 may be known for an analyte that is combined with a dopant 332 (shown in FIG. 3). For example, one of the peaks 840 may correspond to the detection of an analyte combined with a dopant 332 in the field compensation ion mobility spectrometer 102. The presence of the analyte in the sample 108 (shown in FIG. 1) may be determined by examining the height, width and position of the peak 840 at a location 826 along the first axis 812.

In some cases, the use of a dopant 332 reduces the number of missed detections of a particular analyte or ion 338 and the number of false positives of a particular analyte or ion 338. For example, an ion of interest that is obtained from a particular analyte may have a peak 836 in a location 822 along the first axis 812 in the spectrum 810. The peak 836 of this ion of interest may be close to another peak of a second ion along the first axis 812. The second ion may be obtained from an analyte that is not an analyte of interest. If the peak 836 of the ion of interest and the peak of the second ion are too close together along the first axis 812, the presence of the ion of interest may be missed or mistaken for the presence of the second ion. However, combining the dopant 332 with the analyte of interest may move the location of the peak of the ion of interest along the first axis 812. Additionally, combining the dopant 332 with the analyte of interest may obscure the peaks of ions that are not of interest. For example, combining the dopant 332 with the analyte of interest may lead to the formation of peak 840 associated with the ion of interest at location 826 along the first axis 812. This other location 826 may be far enough away from other peaks 828 through 836 to avoid missing the presence of the ion of interest.

Similarly, a location 818 of a peak 832 along the first axis 812 may be known for an ion fragment measured by the mass spectrometer 104. For example, certain ones of neutrals and the ions 338 may generate particular ion fragments when the ions 338 and/or neutrals are struck by the electrons 710 emitted by the electron emitter 706 in the mass spectrometer 104 (shown in FIG. 1). If the shape and location 818 of the peak 832 that corresponds to one of the ion fragments associated with a particular ion 338 is known and the peak corresponding to the ion 338 is found in the spectrum 810, the presence of the particular ion 338 may be confirmed based on the peak of the ion fragment in combination with a characteristic pattern of other fragments and the molecular ion (if present). If a molecular ion is not present, then a well defined pattern of all other related ions and fragments (including the dopant related ions), identified by field compensation ion mobility spectrometry and mass spectrometry may be used.

Based on the relative height of the peaks 828 through 840 of known ions 338, including molecular ions, ion fragments, and ions 338 formed from combinations of a dopant 332 and an analyte, and any other ions 338 relevant the analyte of interest, the presence of various analytes of interest in the sample 108 (shown in FIG. 1) may be determined. As described above, the computing device 112 may compare the spectra 810 created by the field compensation ion mobility spectrometer 102 and the mass spectrometer 104 to determine if a particular peak is found in each spectrum 810. The peak may correspond to ions obtained from a particular analyte of interest. The computing device 112 examines the spectrum 810 produced by each of the field compensation ion mobility spectrometer 102 and the mass spectrometer 104 to determine if both spectra 810 have a peak that matches the peak of the analyte of interest. For example, the computing device 112 examines the spectra 810 to determine whether each spectrum 810 has a peak at the same location, with the same or similar height, width and/or shape as the peak of an analyte of interest, and being a part of the same pattern of peaks (if detection of multiple peaks is possible). The computing device 112 notifies a user if a particular peak 840 that is associated with an analyte of interest is found in a spectrum 810 generated by each of the spectrometers 102, 104. A special emphasis is placed on identifying the molecular peak(s) (if available) in spectra from both spectrometers.

Optionally, if the peak 840 for an analyte of interest is found in only one of the two spectra 810 generated by the spectrometers 102, 104, (for example on the mass spectrometer spectrum), then the analyte of interest is in the sample 108 if the peak represents the molecular ion of the analyte and if there is an additional fragment, a dopant-related peak or any other analyte of interest related peak(s) in the mass spectrum 810. If no molecular ion peak is present, the analyte of interest may be determined to be in the sample 108 if one or more other peaks in the mass spectrum 810 correspond to a known pattern of peaks that is associated with the analyte of interest, for example, the ion fragment and/or dopant-related peaks in the mass spectrum 810 may correspond to a known pattern of ion fragment and/or dopant-related peaks commonly associated with the analyte of interest. The pattern of peaks that is associated with the analyte of interest is a pattern that is obtained from one or more mass and ion mobility spectra that were previously obtained from the analyte of interest in one embodiment.

Figure 9:
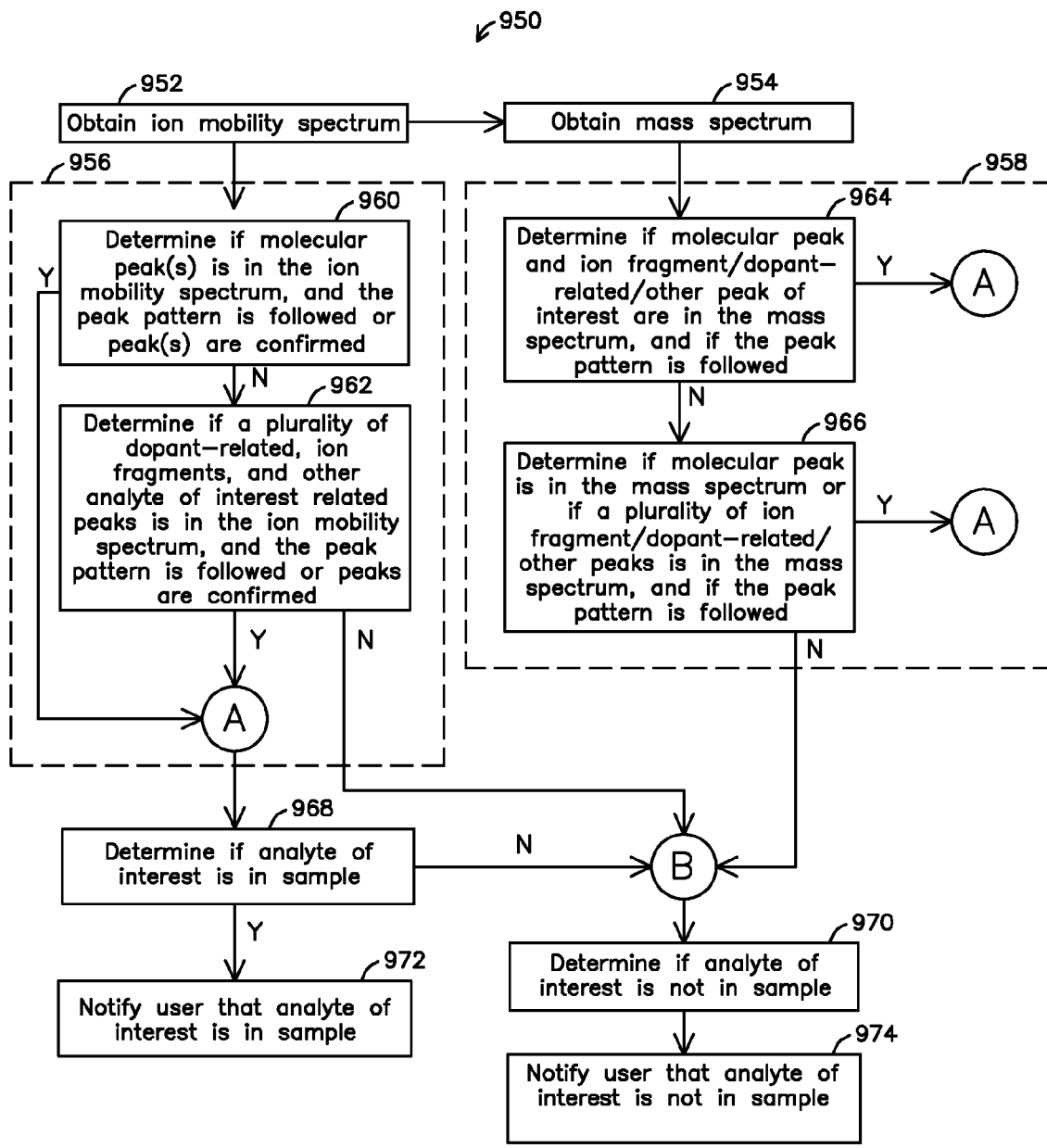
FIG. 9 is a flowchart of a method for detecting the presence of an analyte of interest in a sample according to one embodiment.

FIG. 9 is a flowchart of a method 950 for detecting the presence of an analyte of interest in a sample according to one embodiment. While the various functional blocks of the method 950 are shown and described herein in one or more orders, various embodiments of the method 950 may switch the order of two or more of the functional blocks and/or skip one or more of the functional blocks. Additionally, two or more of the functional blocks may occur simultaneously or concurrently with one another. At 952, a first spectrum is obtained for a set of ions by a field compensation ion mobility spectrometer. For example, an ion mobility spectrum 810 may be obtained by the field compensation ion mobility spectrometer 102 for ions obtained from a sample 108. At 954, a second spectrum is obtained for ions emitted from the field compensation ion mobility spectrometer, as described above. For example, a mass spectrum 810 may be obtained by the mass spectrometer 104 for at least some of the ions exiting the field compensation ion mobility spectrometer 102 after 952. As described above, the field compensation ion mobility spectrometer may filter out ions that are not associated with an analyte of interest.

The method 950 analyzes the spectra obtained by the field compensation ion mobility spectrometer and the mass spectrometer at 952 and 954 according to a plurality of analysis paths 956, 958. The ion mobility spectrum analysis path 956 analyzes the spectrum obtained by the field compensation ion mobility spectrometer while the mass spectrum analysis path 958 analyzes the spectrum obtained by the mass spectrometer. In one embodiment, the computing device 112 performs one or more of the actions described in the functional blocks 960, 962, 964, 966, 968, 970, 972, and 974 shown in the FIG. 9 and described below.

A plurality of the actions described in connection with the functional blocks in the analysis paths 956, 958 are performed concurrently in one embodiment. For example, at least one of the functional blocks 960, 962 in the ion mobility spectrum analysis path 956 may occur for a time period that overlaps with the time period in which at least one of the functional blocks 964, 966 in the mass spectrum analysis path 958 occurs. Alternatively, a plurality of the actions described in connection with the functional blocks in the analysis paths 956, 958 is performed simultaneously in one embodiment. For example, at least one of the functional blocks 960, 962 in the ion mobility spectrum analysis path 956 may occur during the same time period that in which at least one of the functional blocks 964, 966 in the mass spectrum analysis path 958 occurs. In another embodiment, the actions described in the ion mobility spectrum analysis path 956 occur prior to the actions described in the mass spectrum analysis path 958.

In the ion mobility spectrum analysis path 956, a determination is made as to whether a molecular peak is in the ion mobility spectrum at 960. For example, the ion mobility spectrum obtained at 952 is examined to determine if the molecular peak(s) of interest is in the spectrum and to determine if the peak pattern is followed or peak(s) are confirmed. The molecular peak(s) of interest may correspond to the molecular peak(s) for a particular analyte of interest. For example, the determination made at 960 may examine whether a particular molecular peak that is associated with an analyte of interest is in the ion mobility spectrum and if the peak pattern is followed or peak(s) is confirmed. The detection of a molecular peak in the ion mobility spectrum at 960 is confirmed using one or more of methods 1250, 1550 (or subparts thereof) shown and described below in FIGS. 12 and 15 in one embodiment. If the molecular peak(s) of interest was found and the pattern was followed or the peak(s) was confirmed in the ion mobility spectrum at 960, the method 950 proceeds to A between 960 and 968. If no molecular peak of interest was found at 960 or the peak(s) was found but pattern was not followed or the peak(s) could not be confirmed then the method 950 proceeds between 960 and 962.

At 962, a determination is made as to whether a plurality of dopant-related peaks, ion fragment peaks, and other analyte of interest related peaks is found in the ion mobility spectrum obtained at 952. For example, at 962 the ion mobility spectrum obtained at 952 is examined to determine if at least one dopant-related peak, at least one ion fragment peak, and at least one other analyte of interest related peak, a plurality of dopant-related peaks, and/or a plurality of ion fragment peaks, and/or a plurality of other analyte of interest related peaks appear in the ion mobility spectrum, and the peak pattern is followed or the peaks are confirmed. As described above, one or more peaks in the ion mobility spectrum may be associated with one or more dopants that preferentially chemically react or combine with an analyte of interest in the sample being examined. The ion fragment peaks include peaks in the ion mobility spectrum that are associated with ion fragments of an analyte of interest. Additionally, there may be other analyte of interest related peaks in ion mobility spectrum. The detection of a plurality of dopant-related, and/or ion fragment peaks, and/or other analyte of interest related peaks in the ion mobility spectrum at 962 is confirmed using one or more of the methods 1250, 1550 (or subparts thereof) shown and described below in FIGS. 12 and 15 in one embodiment. If a plurality of dopant-related, and/or ion fragment, and/or other analyte of interest related peaks was found in the ion mobility spectrum, and the peaks followed the pattern of peaks or were determined to be confirmed at 962, the method 950 proceeds to A between 962 and 968. If a plurality of dopant-related and/or ion fragment peaks, and/or other analyte of interest related peaks was not found at 962 or these peaks did not follow the pattern and the presence of these peaks could not be confirmed, then the method 950 proceeds to B between 962 and 970.

In the mass spectrum analysis path 958, a determination is made at 964 as to whether (i) a molecular peak of interest and at least one ion fragment/dopant-related or other analyte of interest related peak are in the mass spectrum that was obtained at 954 and (ii) the molecular peak and ion fragment/dopant-related/other analyte of interest related peak(s) correspond to a known peak pattern. For example, the mass spectrum is examined to determine if a molecular peak corresponding to an analyte of interest and if an ion fragment/dopant-related/other peak also corresponding to the analyte of interest are in the mass spectrum obtained at 954. If the molecular and ion fragment/dopant-related/other peaks are found, a determination also is made as to whether the molecular and ion fragment/dopant-related/other peaks correspond or match a pattern of peaks associated with an analyte of interest. As described above, an analyte of interest may be associated with a pattern of molecular peaks, ion fragment peaks and/or dopant-related peaks/other analyte of interest related peaks. This pattern may be considered a peak "fingerprint" for the analyte of interest. The pattern includes the relative locations of the peaks with respect to one another and the relative intensities, or heights, of the peaks. If the molecular and ion fragment/dopant-related/other peaks are in the mass spectrum and the peaks match or correspond to the peak pattern associated with an analyte of interest, the method 950 proceeds to A between 964 and 968. If the molecular and ion fragment/dopant-related/other peaks are not in the mass spectrum or the peaks do not match or correspond to the peak pattern associated with an analyte of interest, the method 950 proceeds from 964 to 966.

At 966, a determination is made as to whether a molecular peak associated with an analyte of interest or a plurality of ion fragment/dopant-related/other peaks associated with the analyte of interest is in the mass spectrum obtained at 954, and if the molecular peak or plurality of ion fragment/dopant-related/other peaks associated with the analyte of interest correspond to the pattern of peaks associated with the analyte of interest. If the molecular peak or plurality of ion fragment/dopant-related/other peaks is found, and the molecular peak or ion fragment/dopant-related/other peaks correspond to the peak pattern associated with the analyte of interest, the method 950 proceeds to A between 966 and 968. If the molecular peak or plurality of ion fragment/dopant-related/other peaks is not found, or the molecular peak or ion fragment/dopant-related/other peaks do not correspond to the peak pattern associated with the analyte of interest, the method 950 proceeds to B between 966 and 970.

At 968, a determination is made as to whether the analyte of interest is in the sample being examined by the method 950. This determination is based on one or more of the results from the decisions and determinations made at one or more of 960, 962, 964, and 966. In one embodiment, if the molecular and ion fragment/dopant-related/other peaks associated with the analyte of interest are found in the mass spectrum and these peaks correspond to the peak pattern associated with the analyte of interest (as determined at 964), then the analyte of interest is determined to be in the sample at 968 and the method 950 proceeds to 972. The ion mobility spectrum 810 that is obtained by the field compensation ion mobility spectrometer at 952 and examined at 960 and/or 962 can be used in conjunction with the mass spectrum 810 to confirm or reinforce the detection of an analyte of interest in the sample. For example, the finding of a molecular peak and ion fragment/dopant-related/other peaks in the mass spectrum at 964 may be further reinforced if the molecular peak and/or dopant related peaks and ion fragment peaks or any other analyte of interest related peaks were found in the ion mobility spectrum 810 at 960 and/or 962. On the other hand, if the molecular and ion fragment/dopant-related/other peaks associated with the analyte of interest are not found in the mass spectrum or these peaks do not correspond to the peak pattern associated with the analyte of interest (as determined at 964 and 966), then the analyte of interest is not determined to be in the sample at 970 and the method 950 proceeds between 970 and 974.

In another embodiment, if (i) it is determined at 968 that the molecular peak or the cluster of the molecular peak is found in the ion mobility spectrum 810 (as determined at 960) and the presence of the molecular peak or the molecular peak cluster is confirmed using one or more of the methods 1250, 1550 shown in FIGS. 12 and 15 and described below, (ii) the molecular peak or a plurality of ion fragment/dopant-related/ others peaks associated with the analyte of interest is found in the mass spectrum (as determined at 966), and (iii) the molecular peak or ion fragment/dopant-related/other peaks in the mass spectrum correspond to the known peak pattern of the analyte of interest in the mass spectrum, then the analyte of interest is determined to be in the sample at 968 and the method 950 proceeds between 968 and 972. For example, the presence of a molecular peak or its cluster in the ion mobility spectrum 810, and the presence of the molecular peak or ion fragment/dopant-related/other peaks in the mass spectrum 810 may be reinforced by the detection of additional peaks that follow a pattern associated with the analyte of interest in the ion mobility spectrum 810. On the other hand, if (i) the molecular peak associated with the analyte of interest is not found in the ion mobility spectrum (as determined at 960), (ii) the molecular peak in the ion mobility spectrum does not fit the peak pattern associated with the analyte of interest, (iii) the molecular peak or a plurality of ion fragment/dopant-related/other peaks associated with the analyte of interest is not found in the mass spectrum (as determined at 964, and 966), or (iv) the molecular peak or ion fragment/dopant-related/other peaks in the mass spectrum do not correspond to the peak pattern of the analyte of interest (as determined at 964, and 966), then the analyte of interest is determined to not be in the sample at 970 and the method 950 proceeds from 970 to 974. For example, the operations performed at 966 allow for a scenario where a molecular ion peak is not found in the mass spectrum. In such a situation, a plurality of ion fragment peaks and/or dopant-related peaks or any other analyte of interest related peak(s) in mass spectrum may be examined to determine if they match a known peak pattern, and the supporting confirmed peaks in ion mobility spectrum are needed, including the molecular peak. In one embodiment, peaks found in the ion mobility spectrum may be confirmed by one or more of the methods 1250, 1550 described below in connection with FIGS. 12 and 15.

In another embodiment, if it is determined at 968 that a plurality of dopant-related peaks, ion fragment peaks, and other analyte of interest related peaks that corresponds to the analyte of interest is found in the ion mobility spectrum (as determined at 962), the dopant-related peaks and/or ion fragment peaks, and other analyte of interest related peaks in the ion mobility spectrum correspond to the peak pattern associated with the analyte of interest, the molecular peak associated with the analyte of interest or a plurality of ion fragment/dopant-related/other peaks associated with the analyte of interest is in the mass spectrum (as determined at 966), and the molecular peak and/or ion fragment/dopant-related or any possible peaks of interest in the mass spectrum correspond to the peak pattern associated with the analyte of interest (as determined at 966), then the analyte of interest is determined to be in the sample at 968 and the method 950 proceeds between 968 and 972. On the other hand, if a plurality of dopant-related peaks, ion fragment peaks, and any possible peaks of interest that corresponds to the analyte of interest is not found in the ion mobility spectrum (as determined at 962), the dopant-related peaks and/or ion fragment peaks or any other peaks of interest in the ion mobility spectrum do not correspond to the peak pattern associated with the analyte of interest, the molecular peak associated with the analyte of interest or a plurality of ion fragment/dopant-related/other peaks associated with the analyte of interest is not in the mass spectrum (as determined at 966), or the molecular peak and/or ion fragment/dopant-related/other peaks, in the mass spectrum do not correspond to the peak pattern associated with the analyte of interest (as determined at 966), then the analyte of interest is determined to not be in the sample at 970 and the method 950 proceeds between 970 and 974.

In one embodiment, at 970, it is determined that the analyte of interest is not present in the sample if (i) no molecular peak or dopant-related peak of the analyte of interest (including monomers, dimers, and trimers of the molecular peak) and ion fragment peaks, and any other peaks of interest, are found in the ion mobility spectrum during the operations performed at 960 and 962 and (ii) no molecular peak or ion fragment/dopant-related/other peaks are found in the mass spectrum during the operations performed at 964 and 966. In another example, at 970, it is determined that the analyte of interest is not present in the sample if the peaks detected in the ion mobility spectrum during the operations performed at 960 and 962 and the peaks detected in the mass spectrum during the operations performed at 964 and 966 do not follow their known patterns, and the ion mobility peaks cannot be confirmed using the methods 1250 and 1550 shown in FIGS. 12 and 15.

In another embodiment, at 968, it is determined that the analyte of interest is present in the sample if at least the molecular and one fragment/dopant-related/other peak are present or, in the case when molecular ion peak is not present but at least 3 ion fragment/dopant-related/other peaks related to the analyte of interest are found in the mass spectrum during the operations performed at 964 and 966, and they follow the known pattern of interest. The presence of any additional peaks in the ion mobility spectrum which follow the known pattern, and/or are confirmed will reinforce the positive decision in this embodiment.

At 972, a user is notified that the analyte of interest is in the sample being examined. For example, the computing device 112 may activate an audible and/or visual alarm to notify a user of the detection system 100 that an analyte of interest is found in the sample 108. At 974, a user is notified that the analyte of interest is not in the sample being examined. For example, the computing device 112 may activate an audible and/or visual alarm to notify a user of the detection system 100 that an analyte of interest is not found in the sample 108.

Figure 10:
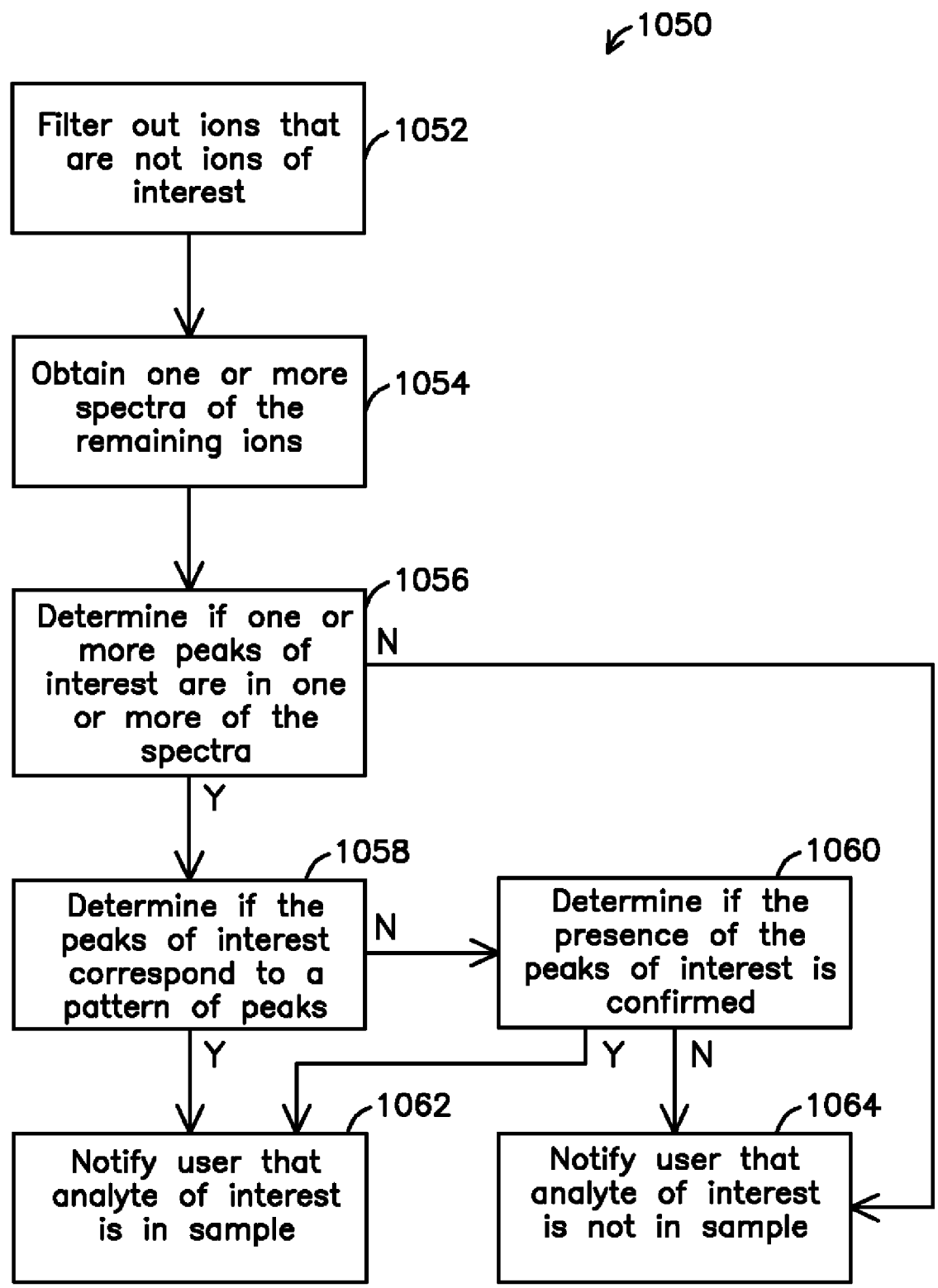
FIG. 10 is a flowchart of a method for detecting the presence of an analyte of interest in a sample according to another embodiment.

FIG. 10 is a flowchart of a method 1050 for detecting the presence of an analyte of interest in a sample according to another embodiment. In one embodiment, a computing device such as the computing device 112 performs one or more of the actions described in the functional blocks 1052, 1054, 1056, 1058, 1060, 1062, and 1064 shown in FIG. 10 and described below. A plurality of the actions described in connection with the functional blocks shown in FIG. 10 is performed concurrently in one embodiment. For example, the functional block 1052 may occur for a time period that overlaps with the functional block 1054, and/or the functional block 1056 may occur for a time period that overlaps with the functional block 1058. Alternatively, a plurality of the actions described in connection with the functional blocks shown in FIG. 10 is performed simultaneously in one embodiment.

At 1052, one or more field compensation ion mobility spectrometers are each used to filter out one or more ions from a set of ions obtained from the sample. For example, one or more field compensation ion mobility spectrometers 102 may be used to filter out one or more ions that are not ions of interest from the sample. Each of the field compensation ion mobility spectrometers 102 may remove additional ions that are not ions of interest. For example, the field compensation ion mobility spectrometers 102 are connected in series with one another in one embodiment.

At 1054, one or more field compensation ion mobility spectrometers obtain one or more spectra of the ions that remain in the set of ions. For example, alter one or more field compensation ion mobility spectrometers 102 filter out at least some of the ions that are not ions of interest, each of one or more additional field compensation ion mobility spectrometers 102 obtains a spectrum of the remaining ions. One or more of the field compensation ion mobility spectrometers that are used to filter out ions that are not ions of interest and one or more of the field compensation ion mobility spectrometers that are used to obtain the spectra may be the same field compensation ion mobility spectrometer.

At 1056, a determination is made as to whether one or more peaks of interest are in the spectrum or spectra obtained at 1054. For example, each of the spectra obtained at 1054 is examined to determine if each spectrum includes one or more peaks of interest. In another example, each of a subset of the spectra obtained at 1054 is examined to determine if each spectrum in the subset includes one or more peaks of interest. In another example, a single spectrum obtained at 1054, such as the last spectrum obtained, is examined to determine if the spectrum includes one or more peaks of interest. The peaks of interest include the molecular peak, ion fragment peaks, dopant-related peaks, and any other peaks that are associated with the analyte of interest, as described above. If one or more peaks of interest are found in the spectrum or spectra, then the method 1050 proceeds between 1056 and 1058. If no peaks of interest are found in the spectrum or spectra, then the method 1050 proceeds between 1056 and 1064.

At 1058, a determination is made as to whether the peaks of interest found at 1056 correspond to a pattern of peaks associated with the analyte of interest. The pattern of peaks may include the known relative locations and intensities, or heights, and shapes of a plurality of peaks of interest associated with the analyte of interest. If the peaks of interest correspond to the pattern of peaks, then the method 1050 proceeds between 1058 and 1062. If the peaks of interest do not correspond to the pattern of peaks, then the method 1050 proceeds between 1058 and 1060. For example, if a molecular peak associated with the analyte of interest and at least one ion fragment peak associated with the analyte of interest and/or dopant-related peak, or any other peak associated with the analyte of interest is found in the spectrum at 1056 and these peaks correspond to the pattern of peaks, then the method proceeds between 1058 and 1062. In another example, if (i) at least one of a plurality of ion fragment peaks associated with the analyte of interest, and if (ii) at least one of a plurality of dopant-related peaks associated with the analyte of interest, are found in the spectrum at 1056 and these peaks correspond to the pattern of peaks, then the method proceeds between 1058 and 1062. In another example, if a molecular peak associated with the analyte of interest is found in the spectrum at 1056 and the presence of the molecular peak is confirmed in 1060, then the method 1050 proceeds between 1060 and 1062. In one embodiment, the presence of the molecular peak may be confirmed using one or more of the methods 1250, 1550 (or subparts thereof) shown and described below in FIGS. 12 and 15.

At 1060, a determination is made as to whether the peaks of interest, found at 1056 and determined to not correspond to the pattern of peaks at 1058, are confirmed. For example, if the presence of a plurality of the peaks of interest found at 1056 but failing to correspond to the pattern of peaks at 1058 is confirmed, then the method 1050 proceeds from 1060 to 1062. If the peaks of interest found at 1056 are not confirmed, then the method 1050 proceeds from 1060 to 1064. In one embodiment, the presence of the peaks of interest may be confirmed using one or more of the methods 1250, 1550 (or subparts thereof) shown and described below in FIGS. 12 and 15.

At 1062, a user is notified that the analyte of interest is in the sample being examined. For example, the computing device 112 may activate an audible and/or visual alarm to notify a user of the detection system 100 that an analyte of interest is found in the sample 108. At 1064, a user is notified that the analyte of interest is not in the sample being examined. For example, the computing device 112 may activate an audible and/or visual alarm to notify a user of the detection system 100 that an analyte of interest is not found in the sample 108.

Figure 11:
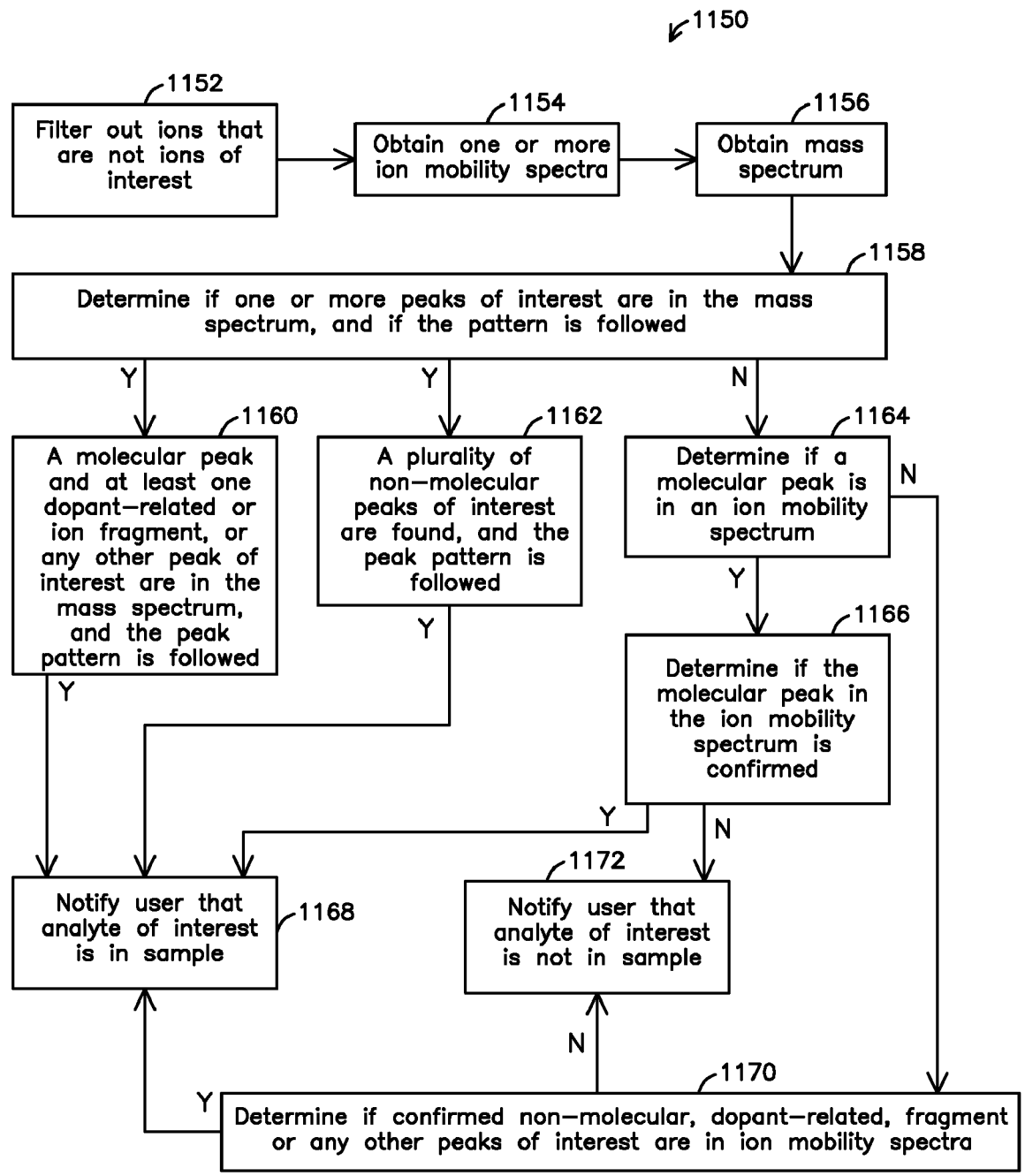
FIG. 11 is a flowchart of a method for detecting the presence of an analyte of interest in a sample according to another embodiment.

FIG. 11 is a flowchart of a method 1150 for detecting the presence of an analyte of interest in a sample according to another embodiment. In one embodiment, a computing device such as the computing device 112 performs one or more of the actions described in the functional blocks 1152, 1154, 1156, 1158, 1160, 1162, 1164, 1166, 1168, 1170, and 1172 shown in FIG. 11 and described below. A plurality of the actions described in connection with the functional blocks shown in FIG. 11 is performed concurrently in one embodiment. For example, one or more of the functional blocks 1158, 1160, 1162, 1164 may occur for a time period that overlaps with the time period during which another one of the functional blocks 1158, 1160, 1162, 1164 occurs. Alternatively, a plurality of the actions described in connection with the functional blocks shown in FIG. 11 is performed simultaneously in one embodiment. For example, one or more of the functional blocks 1158, 1160, 1162, 1164 may occur for the same time period that another one of the functional blocks 1158, 1160, 1162, 1164 occurs.

At 1152, one or more field compensation ion mobility spectrometers are each used to filter out one or more ions from a set of ions. For example, one or more field compensation ion mobility spectrometers 102 connected in a series may be used to filter out one or more ions that are not ions of interest from a set of ions, and to collect ion mobility spectra. The set of ions is obtained from the sample being examined by the method 1150. The ions of interest include ions that are associated with the analyte of interest, or a combination of the analyte of interest and a dopant, as described above. Each of the field compensation ion mobility spectrometers 102 removes additional ions that are not ions of interest.

At 1154, a spectrum such as the spectrum 810 is obtained using one or more of the field compensation ion mobility spectrometers. For example, after several field compensation ion mobility spectrometers 102 have filtered out at least some of the ions that are not ions of interest, each of one or more additional field compensation ion mobility spectrometers 102 filters the sample of ions further, and obtains a spectrum of the remaining ions. This spectrum is referred to as an ion mobility spectrum, as referred to above.

At 1156, a mass spectrometer obtains a spectrum of at least some of the remaining ions that have been filtered at 1152 and 1154. In one embodiment, the mass spectrometer 104 is connected in series with the field compensation ion mobility spectrometers 102 and receives the remaining ions in the set of ions from the last field compensation ion mobility spectrometer 102. The mass spectrometer 104 then obtains a spectrum, such as the spectrum 810, of the remaining ions. This spectrum is referred to as a mass spectrum, as referred to above.

At 1158, a determination is made as to whether a plurality of peaks in the mass spectrum includes peaks of interest. A peak of interest is a peak in the mass spectrum obtained at 1156 that is associated with a molecular peak, an ion fragment peak or a dopant-related or any other peak that is associated with the analyte of interest as described above. If no peaks of interest are found in the mass spectrum at 1158, the method 1150 proceeds between 1158 and 1164. The method 1150 proceeds between 1158 and at least one of 1160, 1162 if one or more peaks of interest are found in the mass spectrum. For example, the method 1150 proceeds between 1158, 1160 and 1168 if a molecular peak of interest and at least one of a dopant-related peak of interest and/or an ion fragment peak of interest or one of any other peaks of interest are found in the mass spectrum, and these peaks of interest follow a pattern of peaks associated with the analyte of interest. The pattern of peaks is a known pattern of peaks in the mass spectrum that is associated with the analyte of interest. For example, the known pattern may include the relative locations, intensities, or heights, and shapes of a plurality of peaks that are known to be associated with the analyte of interest, as described above. In another example, the method 1150 proceeds between 1158, 1162 and 1168 if a plurality of non-molecular peaks of interest is found in the mass spectrum and the non-molecular peaks of interest follow the pattern of peaks associated with the analyte of interest. In one embodiment, the non-molecular peaks of interest include at least two of dopant-related and ion fragment peaks of interest. In another example, if no peaks of interest are found in the mass spectrum or if one or more peaks of interest are found in the mass spectrum, but the peaks do not follow the peak pattern associated with the analyte of interest, then the method 1150 proceeds between 1158 and 1164.

At 1164, a determination is made as to whether a molecular peak of interest is found in the ion mobility spectrum obtained at 1154. For example, a determination may be made as to whether one or more molecular peaks that are associated with the analyte of interest are found in one or more of the ion mobility spectra obtained at 1154. If one or more molecular peaks of interest are found in the ion mobility spectrum or spectra, then the method 1150 proceeds between 1164 and 1166. Conversely, if no molecular peaks of interest are found in the ion mobility spectrum or spectra, then the method 1150 proceeds between 1164 and 170.

At 1166, a determination is made as to whether the molecular peak(s) found in the ion mobility spectrum or spectra at 1164 is confirmed. For example, the presence of the molecular peak of interest in an ion mobility spectrum may be confirmed using one or more of the methods 1250, 1550 (or subparts thereof) shown and described below in FIGS. 12 and 15 in one embodiment. If the presence of the molecular peak of interest in the ion mobility spectrum or spectra is confirmed, then the method 1150 proceeds between 1166 and 1168. Conversely, if the presence of the molecular peak(s) of interest in the ion mobility spectrum or spectra is not confirmed, then the method 1150 proceeds between 1166 and 1172. In some circumstances, the presence of only molecular peak(s) in 1164 and its confirmation in 1166 may be sufficient for the method 1150 to proceed from 1166 to 1168.

At 1168, a user is notified that the analyte of interest is in the sample being examined. For example, the computing device 112 may activate an audible and/or visual alarm to notify a user of the detection system 100 that an analyte of interest is found in the sample 108. At 1170, a determination is made if a plurality of confirmed, non-molecular, dopant-related, fragment, and any other peaks of interest is in ion mobility spectra. If a plurality of these peaks is in the ion mobility spectra, the method 1150 proceeds to 1168. Conversely, if these peaks are not present, the method 1150 proceeds to 1172. At 1172, a user is notified that the analyte of interest is not in the sample being examined. For example, the computing device 112 may activate an audible and/or visual alarm to notify a user of the detection system 100 that an analyte of interest is not found in the sample 108.

Figure 12:
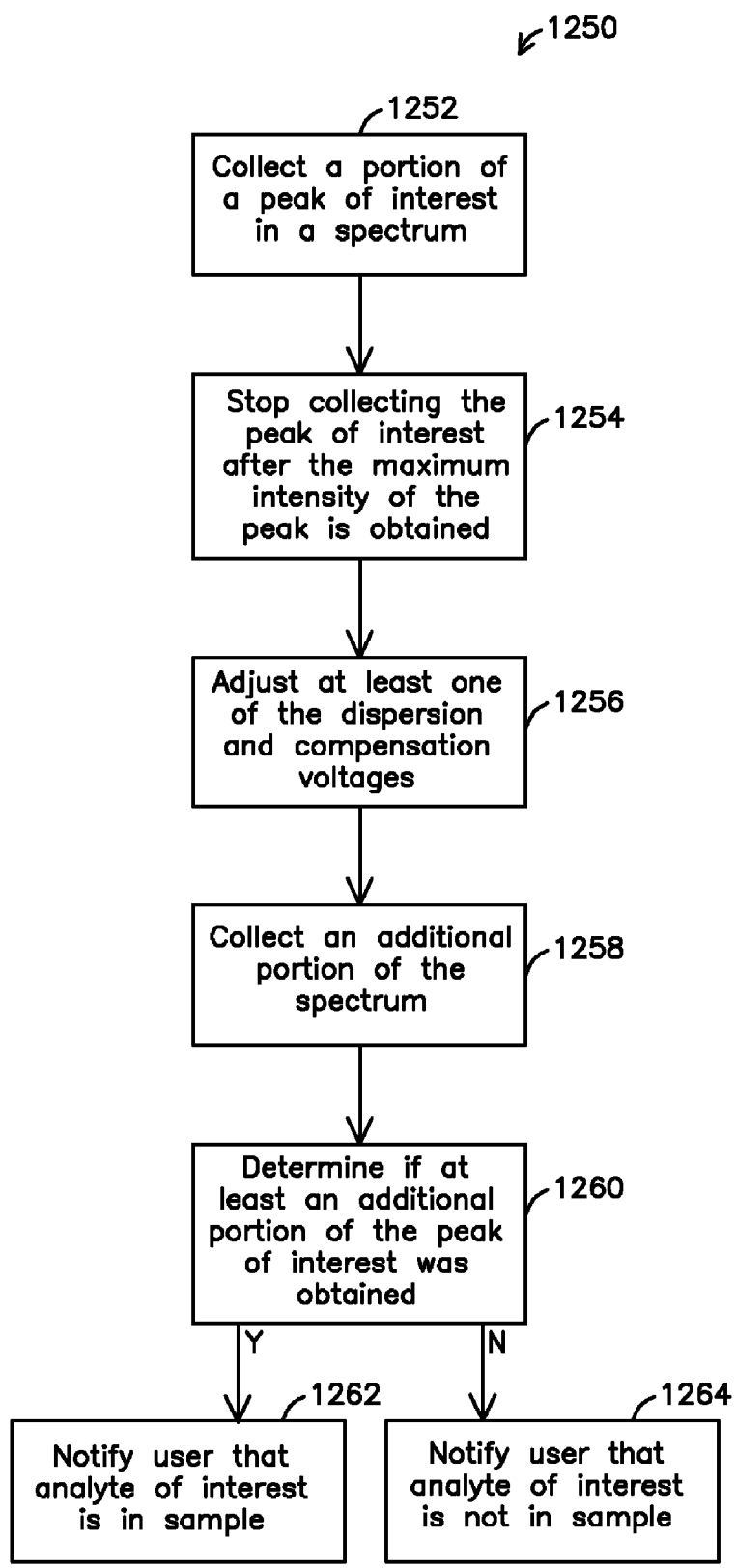
FIG. 12 is a flowchart of a method for confirming the presence of a peak of interest in a spectrum according to one embodiment.

FIG. 12 is a flowchart of a method 1250 for confirming the presence of a peak of interest in a spectrum according to one embodiment. The method 1250 may be used alone or in conjunction with one or more other methods to confirm the presence of a peak of interest in a spectrum obtained by a field compensation ion mobility spectrometer in one embodiment. For example, the method 1250 may be used to confirm the presence of a peak of interest in the spectrum 810 that is obtained using the field compensation ion mobility spectrometer 102. As described above, the peak of interest includes a molecular peak, a dopant-related peak, an ion fragment peak, and any other peak that is associated with an analyte of interest in a sample being examined by the method 1250. In one embodiment, a computing device such as the computing device 112 performs one or more of the actions described in the functional blocks 1252, 1254, 1256, 1258, 1260, 1262, 1264 shown in FIG. 12 and described below.

At 1252, a spectrum is obtained by a field compensation ion mobility spectrometer until at least a portion of a peak of interest appears in the spectrum. For example, measurements for a spectrum may be collected by the field compensation ion mobility spectrometer 102 until at least a portion of a molecular peak of interest is found in the spectrum. The portion of the peak of interest is obtained using an initial field compensation voltage and an initial dispersion voltage in the field compensation ion mobility spectrometer.

At 1254, collection of measurements for the spectrum that is partially obtained at 1252 is stopped after a maximum intensity of the peak of interest is obtained. For example, the spectrum and the peak of interest continues to be obtained or created by the field compensation ion mobility spectrometer until the measured intensity of the peak of interest reaches a maximum and begins to decrease. The field compensation ion mobility spectrometer then stops collecting or obtaining the peak of interest in one embodiment.

Figure 13:
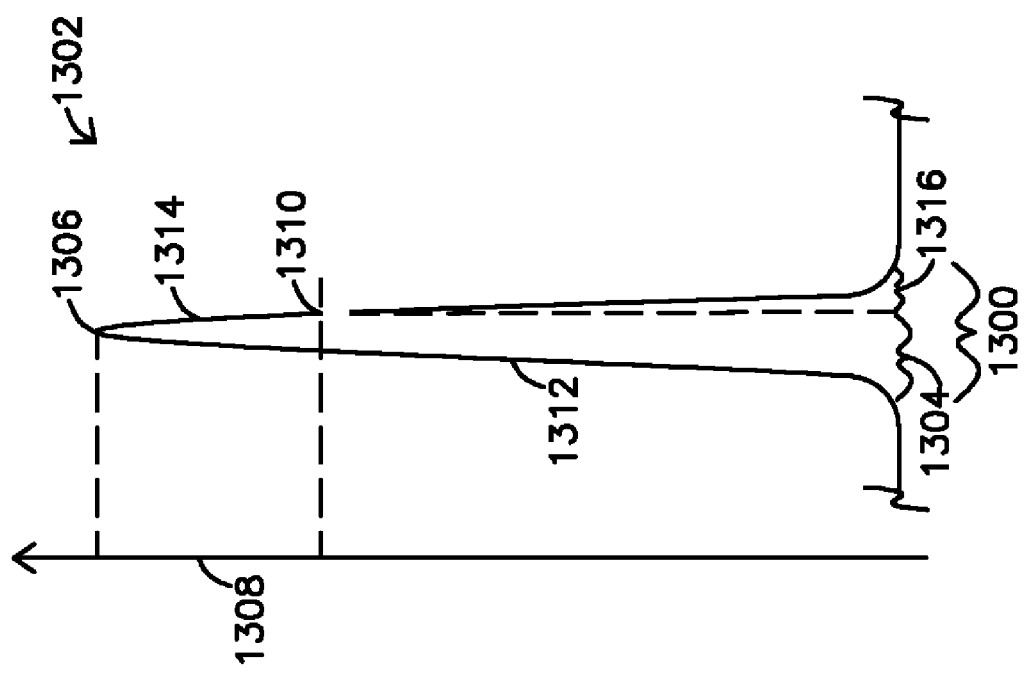
FIG. 13 is a peak of interest in a spectrum that is obtained using a field compensation ion mobility spectrometer in a confirmation mode in accordance with one embodiment.

With continued reference to FIG. 12. FIG. 13 is a peak of interest 1300 in a spectrum 1302 that is obtained using a field compensation ion mobility spectrometer in accordance with one embodiment. The peak of interest 1300 is collected from left to right in FIG. 13 using a field compensation ion mobility spectrometer at an initial dispersion voltage and an initial compensation voltage at 1252 of the method 1250. A first portion 1304 of the peak of interest 1300 is collected at 1252. The first portion 1304 includes an increasing side 1312, a maximum intensity 1306, and a portion of a decreasing side 1314 of the peak of interest 1300. The maximum intensity 1306 is the maximum intensity of the peak of interest 1300 that is measured by the field compensation ion mobility spectrometer, with the intensity of the peak of interest 1300 being measured along a vertical axis 1308. The increasing side 1312 is the portion of the peak of interest 1300 that is collected by the field compensation ion mobility spectrometer prior to collecting the maximum intensity 1306 of the peak of interest 1300. The decreasing side 1314 is the portion of the peak of interest 1300 that is collected by the field compensation ion mobility spectrometer after collecting the increasing side 1312 and the maximum intensity 1306 of the peak of interest 1300.

The peak of interest 1300 is collected at 1252 of the method 1250 such that the increasing side 1312, the maximum intensity 1306 and a portion of the decreasing side 1314 is obtained. At 1254 of the method 1250, collection of the peak of interest 1300 stops at a stopping point 1310. The intensity of the peak of interest 1300 at the stopping point 1310 is less than the maximum intensity 1306. In one embodiment, the intensity of the peak of interest 1300 at the stopping point 1310 is approximately 75% of the maximum intensity 1306. Alternatively, the intensity of the peak of interest 1300 at the stopping point 1310 may be a different percentage or fraction of the maximum intensity 1306.

The method 1250 proceeds between 1254 and 1256. At 1256, at least one of a dispersion voltage and a compensation voltage in a field compensation ion mobility spectrometer is adjusted from the dispersion and/or compensation voltages used to collect a portion of the peak of interest 1300 at 1252. For example, at least one of the dispersion and compensation voltages used by the field compensation ion mobility spectrometer 102 may be changed.

At 1258, an additional portion of the peak of interest 1300 is collected. For example, an additional portion or a remainder 1316 of the peak of interest 1300 may be collected at 1258 using the dispersion and/or compensation voltages that were changed at 1256. While FIG. 13 illustrates the additional portion or remainder 1316 as including the remaining portion of the peak of interest 1300, the additional portion or remainder 1316 may include less than the remaining portion of the peak of interest 1300.

At 1260, a determination is made as to whether the additional portion or remainder 1316 of the peak of interest 1300 fits the peak of interest 1300. For example, the additional portion or remainder 1316 shown in FIG. 13 fits the peak of interest 1300 because the additional portion or remainder 1316 continues the decreasing side 1314 of the peak of interest 1300. Conversely, if the intensity of the peak of interest 1300 after the stopping point 1310 was substantially different than the intensity at the stopping point 1310 and/or did not continue the decrease of the measured intensity of the peak of interest 1300 along the decreasing side 1314, then the additional portion or remainder 1316 would not fit the peak of interest 1300.

Figure 14:
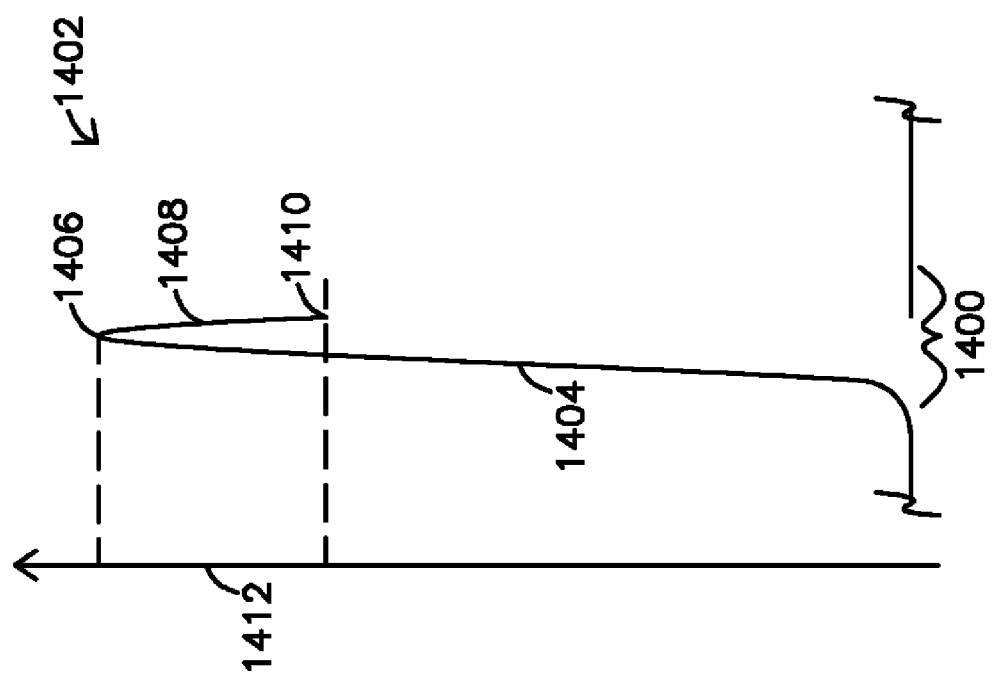
FIG. 14 is another type of peak in a spectrum that is obtained using a field compensation ion mobility spectrometer in accordance with one embodiment.

With continued reference to FIGS. 12 and 13, FIG. 14 is a peak 1400 in a spectrum 1402 that is obtained using a field compensation ion mobility spectrometer. The peak 1400 is similar to the peak of interest 1300, with the exception that the intensity of the peak 1400 does not include the additional portion or remainder 1316 of the peak of interest 1300. For example, the peak 1400 may be collected according to the method 1250 in a manner similar to the peak of interest 1300. An increasing side 1404, maximum intensity 1406 and a portion of a decreasing side 1408 between the maximum intensity 1406 and a stopping point 1410 are collected at 1252. The increasing side 1404, maximum intensity 1406, and the portion of the decreasing side 1408 between the maximum intensity 1406 and the stopping point 1410 may be similar to the increasing side 1312, the maximum intensity 1306 and the portion of the decreasing side 1314 between the maximum intensity 1306 and the stopping point 1310. In contrast, when an additional portion of the peak 1400 is attempted to be collected at 1258, the intensity of the peak 1400 (measured along a vertical axis 1412) substantially drops off and does not continue the gradual decrease of intensity along the decreasing side 1408 as does the additional portion or remainder 1316 of the peak of interest 1300 in FIG. 13.

Returning to 1260 of the method 1250 in FIG. 12, if the additional portion or remainder of the peak of interest is not obtained at 1258 using a different compensation and/or dispersion voltage than was used at 1252, then the method 1250 proceeds between 1260 and 1264. For example, if the peak obtained at 1252 through 1258 appears more similar to the peak 1400 (shown in FIG. 14) than to the peak of interest 1300 (shown in FIG. 13), then the method 1250 proceeds between 1260 and 1264 in one embodiment. Conversely, if the additional portion or remainder of the peak of interest is obtained at 1258, then the method 1250 proceeds between 1260 and 1262.

At 1262, a user is notified that the analyte of interest is in the sample being examined. For example, the computing device 112 may activate an audible and/or visual alarm to notify a user of the detection system 100 that an analyte of interest is found in the sample 108. At 1264, a user is notified that the analyte of interest is not in the sample being examined. For example, the computing device 112 may activate an audible and/or visual alarm to notify a user of the detection system 100 that an analyte of interest is not found in the sample 108.

Figure 15:
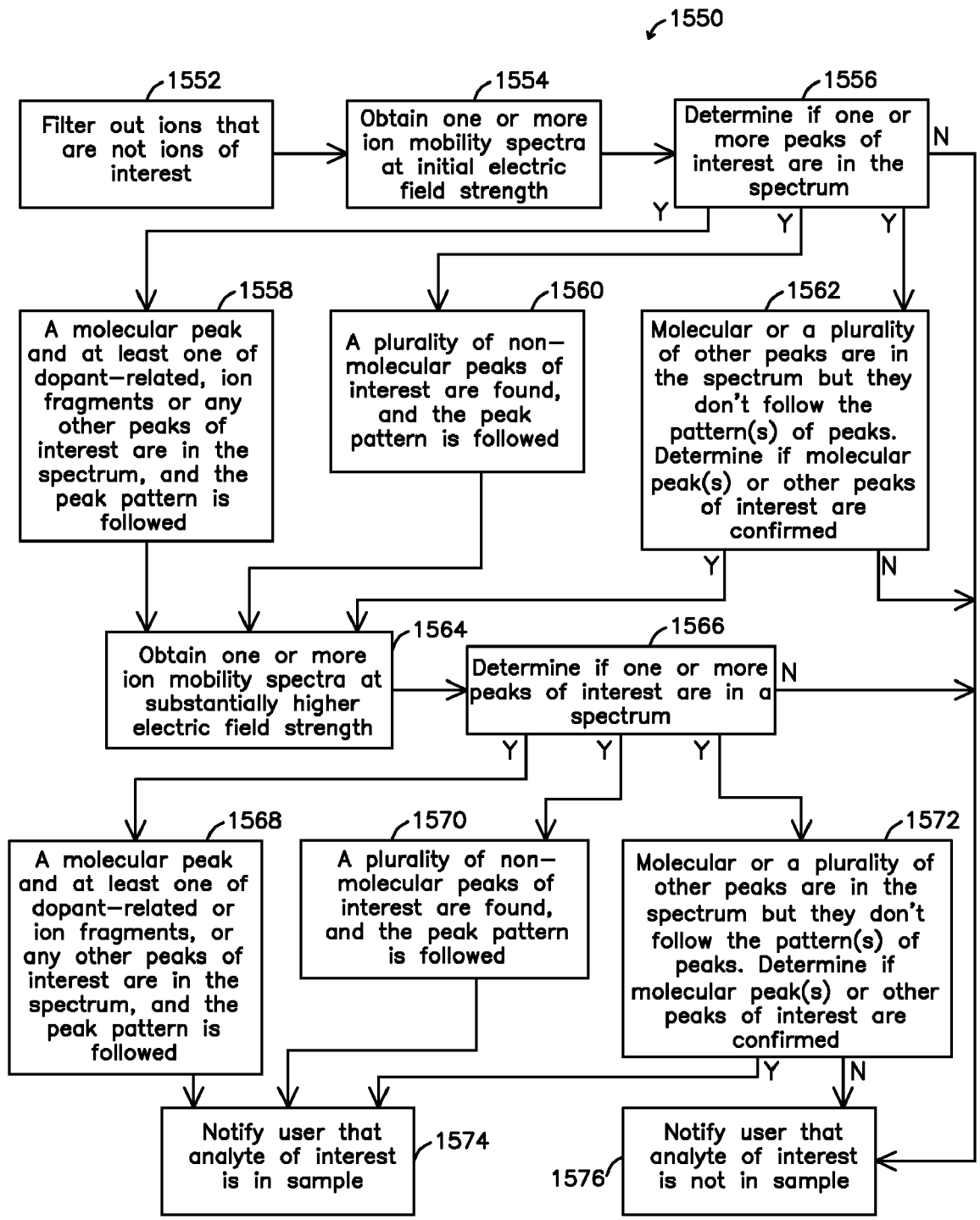
FIG. 15 is a flowchart of a method for detecting and confirming the presence of an analyte of interest in a sample according to another embodiment.

FIG. 15 is a flowchart of a method 1550 for detecting the presence of an analyte of interest in a sample according to another embodiment. In one embodiment, a computing device such as the computing device 112 performs one or more of the actions described in the functional blocks 1552, 1554, 1556, 1558, 1560, 1562, 1564, 1566, 1568, 1570, 1572, 1574, 1576 shown in FIG. 15 and described below. A plurality of the actions described in connection with the functional blocks shown in FIG. 15 is performed concurrently in one embodiment. For example, one or more of the functional blocks 1552, 1554, 1556, 1558, 1560, 1562, 1564, 1566, 1568, 1570, 1572, 1574, 1576 may occur for a time period that overlaps with the time period during which another one of the functional blocks 1552, 1554, 1556, 1558, 1560, 1562, 1564, 1566, 1568, 1570, 1572, 1574, 1576 occurs. Alternatively, a plurality of the actions described in connection with the functional blocks shown in FIG. 15 is performed simultaneously in one embodiment. For example, one or more of the functional blocks 1552, 1554, 1556, 1558, 1560, 1562, 1564, 1566, 1568, 1570, 1572, 1574, 1576 may occur for the same time period that another one of the functional blocks 1552, 1554, 1556, 1558, 1560, 1562, 1564, 1566, 1568, 1570, 1572, 1574, 1576 occurs.

At 1552, one or more field compensation ion mobility spectrometers are each used to (liter out one or more ions from a set of ions obtained from the sample. For example, one or more field compensation ion mobility spectrometers 102 may be used to filter out one or more ions that are not ions of interest from the sample. Each of the field compensation ion mobility spectrometers 102 may remove additional ions that are not ions of interest. For example, the field compensation ion mobility spectrometers 102 are connected in series with one another in one embodiment.

At 1554, one or more field compensation ion mobility spectrometers obtain one or more spectra of the ions that remain in the set of ions at an initial electric field strength. For example, after one or more field compensation ion mobility spectrometers 102 filter out at least some of the ions that are not ions of interest, each of one or more additional field compensation ion mobility spectrometers 102 obtains a spectrum of the remaining ions using an initial electric field strength between the first and second electrode plates 316 and 318 (shown in FIG. 4). One or more of the field compensation ion mobility spectrometers that are used to filter out ions that are not ions of interest and one or more of the field compensation ion mobility spectrometers that are used to obtain the spectra may be the same field compensation ion mobility spectrometer.

At 1556, a determination is made as to whether a plurality of peaks of interest are in the spectrum or spectra obtained at 1554 and whether these peaks of interest follow a pattern of peaks associated with the analyte of interest. For example, each of the spectra obtained at 1554 is examined to determine if each spectrum includes a plurality of peaks of interest. In another example, each of a subset of the spectra obtained at 1554 is examined to determine if each spectrum in the subset includes a plurality of peaks of interest. In another example, a single spectrum obtained at 1554, such as the last spectrum obtained, is examined to determine if the spectrum includes a plurality of peaks of interest. The peaks of interest may include one or more of a molecular peak, ion fragment peaks, dopant-related peaks, and any other peaks that are associated with the analyte of interest, as described above. If a plurality of peaks of interest is found in the spectrum or spectra and the peaks follow the pattern of peaks, then the method 1550 proceeds between 1556 and 1564 through one or more of 1558 and 1560. On the other hand, if a plurality of peaks of interest is not found in the spectrum or spectra, the method 1550 proceeds from 1556 to 1576. In another example, if the peaks are found in the spectrum but the peaks do not follow the pattern(s) of peaks, then the method 1550 proceeds between 1556 and 1562.

For example, if a molecular peak of interest and at least one dopant-related peak of interest and/or ion fragment peak of interest, and/or any other peak of interest are found in the ion mobility spectrum obtained at 1554 and these peaks of interest follow a pattern of peaks associated with the analyte of interest then the method 1550 proceeds between 1556, 1558 and 1564. In another example, if a plurality of non-molecular peaks of interest is found in the ion mobility spectrum obtained at 1554 and these peaks of interest follow a pattern of peaks associated with the analyte of interest, then the method 1550 proceeds between 1556, 1560 and 1564. The non-molecular peaks may include a plurality of dopant-related, ion fragment peaks, and any other peaks associated with the analyte of interest. In another example, if only a single molecular peak of interest is found in the spectrum or spectra obtained at 1554, or if a plurality of peaks of interest is found in the spectrum or spectra obtained at 1554 but these peaks do not follow the pattern of peaks associated with the analyte of interest, then the method 1550 proceeds between 1556 and 1562.

At 1562, a determination is made as to whether the single molecular peak of interest or the plurality of peaks of interest (that do not follow the pattern of peaks) found at 1556 are confirmed. The molecular peak of interest or plurality of peaks of interest is confirmed by the method 1250 shown in FIG. 12 and described above in one embodiment. Such confirmation procedure 1250 can be implemented concurrently or simultaneously with the collection of peaks at 1554 where the peaks may be obtained using compensation voltages of interest. If the molecular peak or plurality of peaks of interest is confirmed, the method 1550 proceeds between 1562 and 1564. If the molecular peak or plurality of peaks of interest is not confirmed, the method 1550 proceeds between 1562 and 1576.

At 1564, one or more field compensation ion mobility spectrometers obtain one or more spectra al substantially higher electric field strength. For example, the same or a different field compensation ion mobility spectrometer used to obtain the spectrum or spectra at 1554 at the initial electric field strength is used to obtain another spectrum or spectra of the ions at an electric field strength that is at least four times greater than the initial electric field strength used at 1554. In one embodiment, the second electric field strength is at least four times greater than the initial electric field strength. For example, the initial electric field strength used at 1554 may be on the order of 20,000 Volts per centimeter while the electric field strength used at 1564 may be on the order of 100,000 Volts per centimeter. Alternatively, different electric field strengths may be used for the initial and/or for the substantially higher electric field strengths. The second electrical field strength used at 1554 may not differ as much from the initial field strength as the second electrical field strength used at 1564 where another confirmation method is used.

In another embodiment, the analysis performed at 1564 can be performed at 1554 using the same or different field compensation ion mobility spectrometer that is in series with the initial field compensation ion mobility spectrometer, while using a portion of ions formed in the initial FCIMS. In a still another embodiment, when the same type of peak is expected at the substantially higher electric field strength, the analysis 1564 can be done in 1554 using the confirmation method 1250 of a partial peak collection, described in FIG. 12. In such case, the substantially higher electric field becomes the second electric field, used to collect the remaining portion of the peak.

At 1566, a determination is made as to whether a plurality of peaks of interest are in the spectrum or spectra obtained at 1564 and whether these peaks of interest follow a pattern of peaks associated with the analyte of interest. For example, each of the spectra obtained at 1564 is examined to determine if each spectrum includes a plurality of peaks of interest. In another example, each of a subset of the spectra obtained at 1564 is examined to determine if each spectrum in the subset includes a plurality of peaks of interest. In another example, a single spectrum obtained at 1564, such as the last spectrum obtained, is examined to determine if the spectrum includes a plurality of peaks of interest. The peaks of interest may include one or more of a molecular peak, ion fragment peaks, dopant-related peaks, and any other peaks that are associated with the analyte of interest, as described above. If a plurality of peaks of interest is found in the spectrum or spectra and the peaks follow the pattern of peaks, then the method 1550 proceeds between 1566 and 1574 through one or more of 1568 and 1570. On the other hand, if a plurality of peaks of interest is not found in the spectrum or spectra, the method 1550 proceeds between 1566 and 1576. In another example, if the peaks in 1566 do not follow the pattern of peaks, then the method 1550 proceeds between 1566 and 1572.

For example, if a molecular peak of interest and at least one dopant-related peak of interest and/or ion fragment peak of interest, and/or any other peak(s) are found in the ion mobility spectrum obtained at 1564 and these peaks of interest follow a pattern of peaks associated with the analyte of interest, then the method 1550 proceeds between 1566, 1568 and 1574. In another example, if a plurality of non-molecular peaks of interest is found in the ion mobility spectrum obtained at 1564 and these peaks of interest follow a pattern of peaks associated with the analyte of interest, then the method 1550 proceeds between 1566, 1570 and 1574. The non-molecular peaks may include a plurality of dopant-related and ion fragment peaks, and any other peaks associated with the analyte of interest. In another example, if only a single molecular peak of interest is found in the spectrum or spectra obtained at 1564, or if a plurality of peaks of interest is found in the spectrum or spectra obtained at 1564 but these peaks do not follow the pattern of peaks associated with the analyte of interest, then the method 1550 proceeds between 1566 and 1572.

At 1572, a determination is made as to whether the single molecular peak of interest or the plurality of peaks of interest (that do not follow the pattern of peaks) found at 1566 are confirmed by the method 1250 described in FIG. 12. The molecular peak of interest or plurality of peaks of interest is confirmed by the method 1250 shown in FIG. 12 and described above in one embodiment. If the molecular peak or plurality of peaks of interest is confirmed, the method 1550 proceeds between 1572 and 1574. If the molecular peak or plurality of peaks of interest is not confirmed, the method 1550 proceeds between 1572 and 1576.

At 1574, a user is notified that the analyte of interest is in the sample being examined. For example, the computing device 112 may activate an audible and/or visual alarm to notify a user of the detection system 100 that an analyte of interest is found in the sample 108. At 1576, a user is notified that the analyte of interest is not in the sample being examined. For example, the computing device 112 may activate an audible and/or visual alarm to notify a user of the detection system 100 that an analyte of interest is not found in the sample 108. In one embodiment, the method 1550 provides a process for confirming the presence of one or more peaks in a spectrum. For example, the functional blocks 1556 through 1572 may be used to confirm the presence of one or more peaks by detecting the peaks at an initial electric field strength in a field compensation ion mobility spectrometer and then detecting the peaks (or peaks that are related to the initially detected peaks and that represent new, specific molecules formed only at the substantially higher electric field strength conditions) at a substantially higher electric field strengths in a different (or the same) field compensation ion mobility spectrometer.

Figure 16:
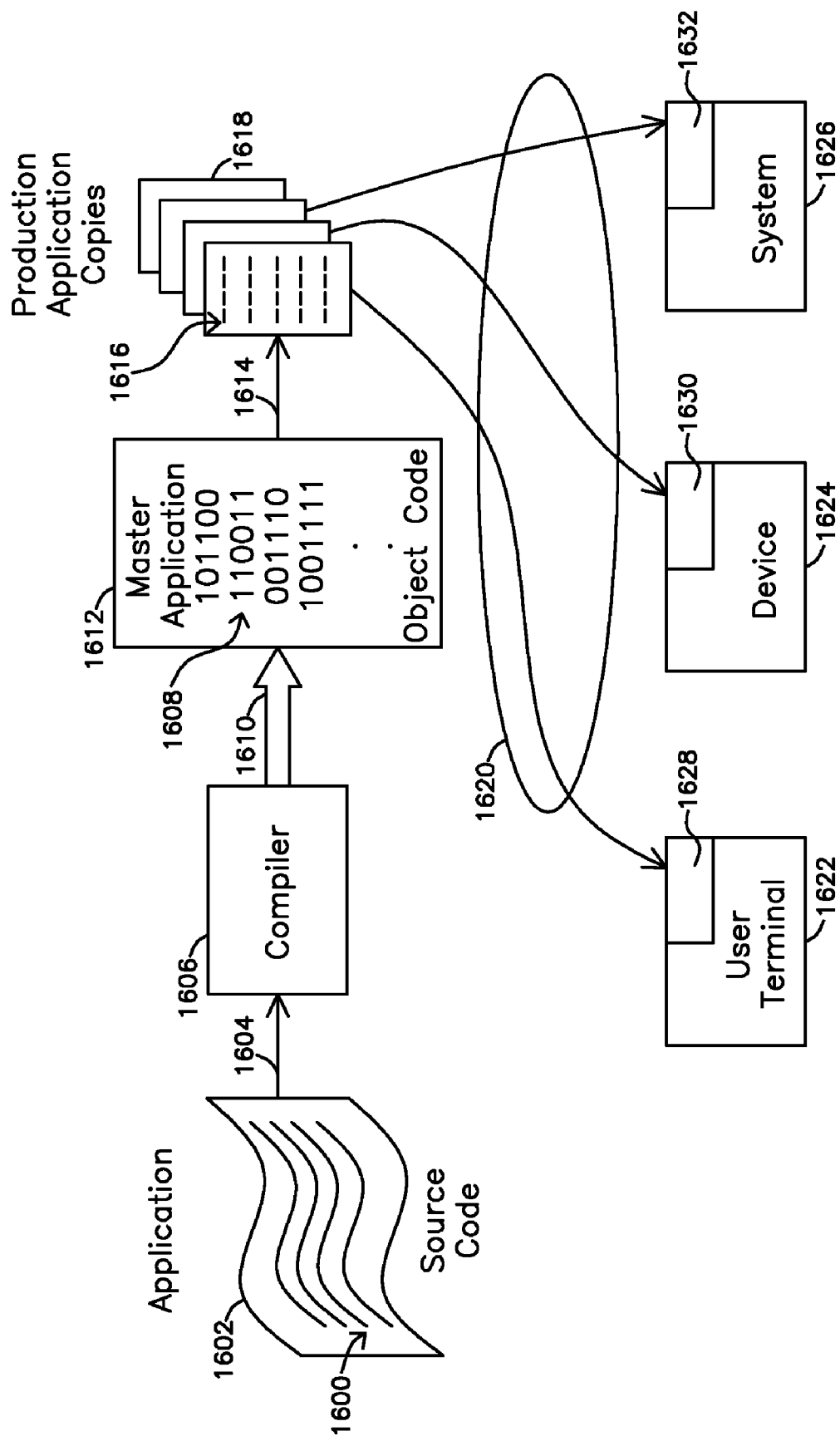
FIG. 16 illustrates a block diagram of exemplary manners in which embodiments of the present invention may be stored, distributed and installed on a computer-readable medium.

FIG. 16 illustrates a block diagram of exemplary manners in which embodiments of the present invention may be stored, distributed and installed on a computer-readable medium. In FIG. 16, the "application" represents one or more of the methods and process operations discussed above. For example, the application may represent the process carried out in connection with FIGS. 1 through 15 as discussed above. As shown in FIG. 16, the application is initially generated and stored as source code 1600 on a source computer-readable medium 1602. The source code 1600 is then conveyed over path 1604 and processed by a compiler 1606 to produce object code 1608. The object code 1608 is conveyed over path 1610 and saved as one or more application masters on a master computer-readable medium 1612. The object code 1608 is then copied numerous times, as denoted by path 1614, to produce production application copies 1616 that are saved on separate production computer-readable medium 1618. The production computer-readable medium 1618 is then conveyed, as denoted by path 1620, to various systems, devices, terminals and the like. In the example of FIG. 16, a user terminal 1622, a device 1624 and a system 1626 are shown as examples of hardware components, on which the production computer-readable medium 1618 are installed as applications (as denoted by 1628 through 1632). For example, the production computer-readable medium 1618 may be installed on the computer device 112 shown in FIG. 1.

The source code may be written as scripts, or in any high-level or low-level language. Examples of the source, master, and production computer-readable medium 1602, 1612 and 1618 include, but are not limited to, CDROM, RAM, ROM, Flash memory, RAID drives, memory on a computer system and the like. Examples of the paths 1604, 1610, 1614, and 1620 include, but are not limited to network paths, the internet, Bluetooth, GSM, infrared wireless LANs, HIPERLAN, 3G, satellite, and the like. The paths 1604, 1610, 1614, and 1620 may also represent public or private carrier services that transport one or more physical copies of the source, master, or production computer-readable medium 1602, 1612 or 1618 between two geographic locations. The paths 1604, 1610, 1614 and 1620 may represent threads carried out by one or more processors in parallel. For example, one computer may hold the source code 1600, compiler 1606 and object code 1608. Multiple computers may operate in parallel to produce the production application copies 1616. The paths 1604, 1610, 1614, and 1620 may be intra-state, inter-state, intra-country, inter-country, intra-continental, inter-continental and the like.

The operations noted in FIG. 16 may be performed in a widely distributed manner world-wide with only a portion thereof being performed in the United States. For example, the application source code 1600 may be written in the United States and saved on a source computer-readable medium 1602 in the United States, but transported to another country (corresponding to path 1604) before compiling, copying and installation. Alternatively, the application source code 1600 may be written in or outside of the United States, compiled at a compiler 1606 located in the United States and saved on a master computer-readable medium 1612 in the United States, but the object code 1608 transported to another country (corresponding to path 1614) before copying and installation. Alternatively, the application source code 1600 and object code 1608 may be produced in or outside of the United States, but production application copies 1616 produced in or conveyed to the United States (for example, as part of a staging operation) before the production application copies 1616 are installed on user terminals 1622, devices 1624, and/or systems 1626 located in or outside the United States as applications 1628 through 1632.

As used throughout the specification and claims, the phrases "computer-readable medium" and "instructions configured to" shall refer to any one or all of (i) the source computer-readable medium 1602 and source code 1600, (ii) the master computer-readable medium and object code 1608, (iii) the production computer-readable medium 1618 and production application copies 1616 and/or (iv) the applications 1628 through 1632 saved in memory in the terminal 1622, device 1624 and system 1626.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and merely are example embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function formal and are not intended to be interpreted based on 35 U.S.C. §112, sixth paragraph, unless and until such claim limitations expressly use the phrase "means for" followed by a statement of function void of further structure.

What is claimed is:

1. A method for detecting an analyte of interest in a sample, the method comprising:
    passing a set of ions obtained from the sample through an ion mobility spectrometer to filter out ions that are not ions of interest and to generate an ion mobility spectrum;
    generating a mass spectrum of at least some of the ions using a mass spectrometer;
    determining that the analyte of interest is in the sample when peaks of interest are found in one or more of the ion mobility spectrum and the mass spectrum, and the peaks of interest follow a predetermined pattern of peaks associated with the analyte of interest; and
    confirming a presence of at least one of the peaks of interest by obtaining an initial portion of the at least one of the peaks of interest using a first dispersion voltage and a first compensation voltage in the ion mobility spectrometer and obtaining an additional portion of the at least one of the peaks of interest using at least one of a different, second dispersion voltage or a different, second compensation voltage in the ion mobility spectrometer.

2. The method of claim 1, wherein the passing operation comprises passing the ions through a plurality of ion mobility spectrometers connected in series with one another.

3. The method of claim 1, wherein the generating operation comprises passing the ions through a plurality of mass spectrometers connected in series with one another.

4. The method of claim 1, wherein the peaks of interest comprise one or more of a molecular peak created from ions associated with a molecule in the analyte of interest, an ion fragment peak created from an ion fragment obtained from the analyte of interest, a dopant-related peak created from a chemical species formed from a reaction between the analyte of interest and a dopant, or any other peak representing the analyte of interest.

5. The method of claim 4, wherein the determining operation comprises determining that the analyte of interest is in the sample when the peaks of interest include the molecular peak and at least one of the ion fragment peak, the dopant-related peak, or any other peak related to the analyte of interest in the mass spectrum.

6. A system for detecting an analyte of interest in a sample, the system comprising:
    an ion mobility spectrometer configured to receive a set of ions obtained from the sample to filter out ions that are not ions of interest and to generate an ion mobility spectrum;
    a mass spectrometer connected in series with the ion mobility spectrometer to receive at least some of the ions from the ion mobility spectrometer and to generate a mass spectrum of the ions received from the ion mobility spectrometer; and
    a computing device for determining that the analyte of interest is in the sample when peaks of interest are found in one or more of the ion mobility spectrum and the mass spectrum and the peaks of interest follow a predetermined pattern of peaks associated with the analyte of interest,
    wherein the ion mobility spectrometer is configured to confirm a presence of at least one of the peaks of interest by obtaining an initial portion of the at least one of the peaks of interest using a first dispersion voltage and a first compensation voltage and obtaining an additional portion of the peak of interest using at least one of a different, second dispersion voltage or a different, second compensation voltage.

7. The system of claim 6, further comprising at least one additional ion mobility spectrometer connected in series with the ion mobility spectrometer and the mass spectrometer, the ions passing through each of the ion mobility spectrometer and the additional ion mobility spectrometer to filter out ions that are not ions of interest and to generate an ion mobility spectrum.

8. The system of claim 6, further comprising at least one additional mass spectrometer connected in series with the ion mobility spectrometer and the mass spectrometer, the ions received by each of the mass spectrometer and the additional mass spectrometer to generate a mass spectrum.

9. The system of claim 6, wherein the peaks of interest comprise one or more of a molecular peak created from ions associated with a molecule in the analyte of interest, an ion fragment peak created from an ion fragment obtained from the analyte of interest, a dopant-related peak created from a chemical species formed from a reaction between the analyte of interest and a dopant, or any other peak related to the analyte of interest.

10. The system of claim 9, wherein the computing device determines that the analyte of interest is in the sample when the peaks of interest include the molecular peak and at least one of the ion fragment peak, the dopant-related peak, and or any other peak related to the analyte of interest in the mass spectrum.

11. A computer-readable storage medium for a computing device configured to determine if an analyte of interest is in a sample, the computer-readable storage medium comprising instructions to direct the computing device to:
    generate one or more of an ion mobility spectrum and a mass spectrum of ions obtained from the sample;
    detect peaks of interest in one or more of the ion mobility spectrum and the mass spectrum;
    determine if the peaks of interest follow a predetermined pattern of peaks associated with the analyte of interest;
    confirm the presence of the peak of interest by obtaining a portion of the peak of interest at a first dispersion voltage and a first compensation voltage in an ion mobility spectrometer and obtaining an additional portion of the peak of interest using one or more of a different, second dispersion voltage or a different, second compensation voltage in the ion mobility spectrometer; and provide a notification that the analyte of interest is in the sample when the peaks of interest follow the predetermined pattern of peaks.

12. The computer-readable storage medium of claim 11, wherein the peaks of interest comprise one or more of a molecular peak created from ions associated with a molecule in the analyte of interest, an ion fragment peak created from an ion fragment obtained from the analyte of interest, a dopant-related peak created from a chemical species formed from a reaction between the analyte of interest and a dopant, or any other peak related to the analyte of interest.

13. The computer-readable storage medium of claim 11, wherein the instructions direct the computing device to provide the notification if one or more of the peaks of interest are in the ion mobility spectrum, the predetermined peak pattern is followed or a presence of at least one of the peaks of interest in the ion mobility spectrum is confirmed.

14. The computer-readable storage medium of claim 13, wherein the instructions direct the computing device to provide the notification if a molecular peak of interest and at least one of an ion fragment peak of interest, a dopant-related peak of interest, or any other peak related to the analyte of interest are found in the mass spectrum, and the predetermined peak pattern is followed.

15. The computer-readable storage medium of claim 13, wherein the instructions direct the computing device to confirm the presence of the peak of interest by obtaining the peak of interest using a first electric field in the ion mobility spectrometer and obtaining the peak of interest or a different peak of interest using a second electric field in the ion mobility spectrometer, the second electric field being at least four times greater than the first electric field.

16. The computer-readable storage medium of claim 11, wherein the peaks of interest comprise a molecular peak of interest and at least one of an ion fragment peak of interest, a dopant-related peak of interest, or another peak of interest detected in the ion mobility spectrum, further wherein the instructions direct the computing device to confirm a presence of the peaks of interest in the ion mobility spectrum.

17. A system for detecting an analyte of interest in a sample, the system comprising:

a first field compensation ion mobility spectrometer ("first FCIMS") configured to receive a set of ions generated from the sample and filtering filter out ions from the set that are not ions of interest and generating a first ion mobility spectrum;

a second field compensation ion mobility spectrometer ("second FCIMS") connected with the first FCIMS, the second FCIMS receiving ions from the first FCIMS to generate a second ion mobility spectrum; and a computing device for analyzing the first and second ion mobility spectra to determine a presence of the analyte of interest in the sample when peaks of interest are in the first and second ion mobility spectra.

18. The system of claim 17, wherein the peaks of interest comprise one or more of a molecular peak created from ions associated with a molecule in the analyte of interest, an ion fragment peak created from an ion fragment obtained from the analyte of interest, a dopant-related peak created from a chemical species formed from a reaction between the analyte of interest and a dopant, or any other peak related to the analyte of interest.

19. The system of claim 17, wherein the computing device determines the presence of the analyte of interest when the peaks of interest follow a predetermined pattern of peaks associated with the analyte of interest.

20. The system of claim 17, wherein the computing device determines the presence of the analyte of interest when the peaks of interest are confirmed by at least one of the first and second FCIMS.

21. The system of claim 20, wherein the at least one of the first and second FCIMS confirms the presence of the analyte of interest by obtaining a first portion of at least one of the peaks of interest using a first electric field and obtaining an additional portion of the peak of interest using a second electric field.

22. The system of claim 17, wherein each of the first and second FCIMS comprise opposing electrode plates configured to generate an electric field through which the ions pass before being detected or filtered by the first and second FCIMS, wherein the electrode plates of the first FCIMS are separated by a different distance than the electrode plates of the second FCIMS.

* * * * *